United States Patent [19]
Elrod et al.

[11] Patent Number: 5,958,747
[45] Date of Patent: Sep. 28, 1999

[54] *ASPERGILLUS ORYZAE* 5-AMINOLEVULINIC ACID SYNTHASES AND NUCLEIC ACIDS ENCODING SAME

[75] Inventors: Susan L. Elrod; Joel R. Cherry, both of Davis, Calif.

[73] Assignee: Novo Nordisk Biotech, Inc, Davis, Calif.

[21] Appl. No.: 09/018,864

[22] Filed: Feb. 5, 1998

Related U.S. Application Data

[62] Division of application No. 08/871,266, Jun. 9, 1997.
[60] Provisional application No. 60/019,399, Jun. 10, 1996.
[51] Int. Cl.$^6$ ............... C12N 9/10; C12N 15/54
[52] U.S. Cl. ............ 435/193; 435/320.1; 435/252.3; 435/254.4; 435/254.21; 435/254.3; 435/254.5; 435/254.6; 435/254.7; 435/254.8; 536/23.2
[58] Field of Search .................. 435/193, 320.1, 435/252.3, 254.11, 254.21, 254.3, 254.4, 254.5, 254.6, 254.7, 254.8; 536/23.2

[56] References Cited

U.S. PATENT DOCUMENTS 4,902,620  2/1990  Bard et al. ............... 435/172.3

FOREIGN PATENT DOCUMENTS 0 238 023  9/1987  European Pat. Off. .

OTHER PUBLICATIONS

Bradshaw et al., Current Genetics, vol. 23, pp. 501–507 (1993).

Urban–Grimal et al., Eur. J. Biochem, vol. 156, pp. 511–519 (1986).

XP 002045204, Asahi Chem Ind. Co. Ltd., Japanese Abstract of J 02167083 (Jun. 7, 1990).

*Primary Examiner*—Charles L. Patterson, Jr.
*Attorney, Agent, or Firm*—Steve T. Zelson; Elias J. Lambiris

[57] ABSTRACT

The present invention relates to *Aspergillus oryzae* 5-aminolevulinic acid synthases and isolated nucleic acid fragments comprising nucleic acid sequences encoding the 5-aminolevulinic acid synthases as well as nucleic acid constructs, vectors, and recombinant host cells comprising the nucleic acid sequences. The invention also relates to methods of producing the 5-aminolevulinic acid synthases.

23 Claims, 13 Drawing Sheets

ACCATTGACTCTCAAGCTATGGATCGTGCTCACCGTCTCGGCCAGACAAGACAGGTCACG 60
GTGTATCGCCTGATTACTCGCGGCACCATTGAGGAGCGTATTCGCAAGCGAGCTTTGCAG 120
AAGGAGGAAGTGCAGCGTGTCGTCATCTCAGGTGGCGCAGCTGGTGGGGTTGACTTCAAT 180
ACTCGCAACCGCGAGAGCCGAACCAAGGACATCGCCATGTGGCTGGCAGATGATGAACAG 240
GCGGAGCTTATTGAGCAAAAGGAGAAGGAAGCGCTGGACCGAGGCGAAGTGTTTGGCGCT 300
AGTAAAGGCGGGAAGAAGGCTGCTCAGAAGAGAAAGAGAGATATCACGCTGGATGATATG 360
TATCATGAAGGTATGTGAATCTGATCAAAGCTCTTCGTTCCGGGGAGGCTTCTGGAAATA 420
GTACTAACCGCGTCAATCTATAGGCGAAGGGAACTTTGACGATGCCAGTGCAAAGCCATC 480
AGGAGCGGCCACTCCTGTGTCGACTGCAGAGAATTTAGGCACCCCATCCTCCACGCCAGT 540
TCCTAAACGAGGACGTGGAAGGGGGACAGGAAAGGGCACGTCTAAAAGAGCCAAAACTAC 600
CAAGGAGAGATTACGTCTCATTGATGGCGACGGAGGCTTAGGGCCTAGTTGATTTAATCG 660
ATCTGTGCCTCAATAATGGACACGGCTGGTTATGGTCATGGCGTTCAGAGATTGCATTTC 720
TTTCCCACCCTTTATCTTTCTTTCTTTCCTCTTAAACCCCTCTTTTTTGTTTTTCTTTTT 780
ATCGGACTTTACTTGTGGGCAGCTTACGTTCTGCCTTGTATTAACAGCATATATTCCTGA 840
TTCCTGATGTACGAAGCGATTTAAGAGTCATTGAAGACGAAGGATGAAACCCGTGGTAAT 900
CAGCCGATAATGGCAAAGAGAAGGAGAAGAAAAAATCAAGTGCGAGTTTTGAAATTGAT 960
GGCAAGATAGACATTGTATCCTGTACCTGTTCTTGGGCTGTGACGGGGGGGGTGAAATTG 1020
ACGGTCATCACCCGGCTATTATTACTATTGTTGTACTGTACATCCGGATCCTGCTGGTCT 1080
GTATCTAGTTAGGGCAATATTCCCCGTCGCCAGGCCTCTTGGGTTATGAATGATTTCATA 1140
GGTGAAGTTTCGTATCCGTACGCACCGAGAGATTTCTTAGTATTACTTGTATTATGAAAA 1200
TGCACTTGCCGAGTTAAGTCCGCCGGCCAATCACGGCGGAGGATATGGTAAGCCGAAAAG 1260
TCTCGCCGAAGTCCCCGACTTACTCTTACTGGAAGTGGCTTAGTGCCCTCAGCGCCCCCT 1320
CGCCCTCAGTCCATCAGCCAGATTGACTCTTATTTCTCTCTCCTCTTCGCCGCGGGTGAC 1380
ATATCCCTCTCCTTCTCCCTCTCCCTCTTGACAACATTTCATCTTCGCTTCCTTTTGTGA 1440
TATAGTCAGTTTCGCTATCCATTGAAGCATCACTCATGGAGTCTCTTCTCCAGCAGTCCC 1500
                                      M  E  S  L  L  Q  S
GGGCGA TGTGCCCGTTCCTTT AAGCGCACATCTCCATCTTCTCTGCGTACGCTGGCAACCG 1560
R  A   M  C  P  F  L   K  R  T  S  P  S  S  L  R  T  L  A  T
CGACTCGACCTAGCACTAGTTCCGGTGGAGGCACTATGTCTAATCTCCAGGTCATTGCCC 1620
 R   L   D   L   A   L   V   P   V   E   A   L   C   L   I   S   R   S   L   P
GTC GCTGCCCTGTCATGA GCAAGGCTCTGGCCGTGCAGAGCGCTCGCATGGCCGGTACCA 1680
 V   R  C  P  V  M    S   K   A   L   A   V   Q   S   A   R   M   A   G   T
AAAGATTCACCTCATGTGCTGCCGGCATCACCGGTCTCGGCAACAAGCATTGCCGTGCTC 1740
 K   R   F   T   S   C   A   A   G   I   T   G   L   G   N   K   H   C   R   A
CTACTGGGAAGAGAACCCTGCACTCCACCTCCGGTAACGGCGCCAATGTGAGCGCAGAGA 1800
 P   T   G   K   R   T   L   H   S   T   S   G   N   G   A   N   V   S   A   E
TCTACAAGAACACCCAGCGAGATCCCGCCGGTTTCTCGAAGATCAAGACCCCTGCCAATG 1860
 I   Y   K   N   T   Q   R   D   P   A   G   F   S   K   I   K   T   P   A   N
CTACCGCCGCTGCCGCTACGTCTGGCCCTCGTCCAGAGGCTCCCGTGGCGAAGCCTTTCA 1920
 A   T   A   A   A   A   T   S   G   P   R   P   E   A   P   V   A   K   P   F
ACTACAATTCTTTCTACAACACCGAATTGGAAAAGAAACACAAGGACAAGTCGTATCGCT 1980
 N   Y   N   S   F   Y   N   T   E   L   E   K   K   H   K   D   K   S   Y   R
ATTTCAACAACATCAATCGTCTCGCTCAGGAGTTTCCCCGGGCTCACACCACATCTGCCG 2040
 Y   F   N   N   I   N   R   L   A   Q   E   F   P   R   A   H   T   T   S   A
AGGAACGTGTGACGGTCTGGTGCTCGAACGATTATCTCGGCATGGGCCGCAACCCCGAGG 2100
 E   E   R   V   T   V   W   C   S   N   D   Y   L   G   M   G   R   N   P   E
TTCTGGCCACCATGCATAAGACATTGGACACCTACGGAGCCGGTGCGGAGGTACTCGCA 2160
 V   L   A   T   M   H   K   T   L   D   T   Y   G   A   G   A   G   G   T   R
ACATTTCAGGTCACAATCAACATGCCGTGAGCCTGGAGAACACCCTGGCCAAATTGCACG 2220
 N   I   S   G   H   N   Q   H   A   V   S   L   E   N   T   L   A   K   L   H
GCAAGGAGGCGGCATTAGTCTTCAGCTCATGCTTCGTGGCTAACGATGCCACCCTCGCAA 2280
 G   K   E   A   A   L   V   F   S   S   C   F   V   A   N   D   A   T   L   A
CCCTGGGTAGCAAGTTGCCCGACTGTGTTATTCTGTCCGATAGCCTGAATCATGCATCGA 2340
 T   L   G   S   K   L   P   D   C   V   I   L   S   D   S   L   N   H   A   S
TGATTCAGGGTATTCGCCATTCAGGCGCCAAGAAAATGGTTTTCAAGCATAATGATCTGG 2400
 M   I   Q   G   I   R   H   S   G   A   K   K   M   V   F   K   H   N   D   L

FIG. 3A

```
TCGACCTTGAGGCCAAGTTGGCAGCTCTACCTCTTCATGTCCCCAAGATTATTGCATTCG 2460
 V  D  L  E  A  K  L  A  A  L  P  L  H  V  P  K  I  I  A  F
AATCAGTTTATAGCATGTGCGGATCTATTGCCCCAATTGAGAAGATCTGTGATCTTGCAG 2520
 E  S  V  Y  S  M  C  G  S  I  A  P  I  E  K  I  C  D  L  A
ACAAGTACGGTGCCATTACTTTCCTGGATGAAGTCCACGCTGTGGGAATGTACGGACCTC 2580
 D  K  Y  G  A  I  T  F  L  D  E  V  H  A  V  G  M  Y  G  P
ACGGAGCAGGTGTGGCAGAGCACCTTGACTATGACATCTATGCTTCCCAAGATACGGTCA 2640
 H  G  A  G  V  A  E  H  L  D  Y  D  I  Y  A  S  Q  D  T  V
ACCCGCGCAGTACTAAGGGAACCGTGATGGACCGAATCGATATTATCACCGGTACTCTGG 2700
 N  P  R  S  T  K  G  T  V  M  D  R  I  D  I  I  T  G  T  L
GCAAGGCCTACGGATGTGTCGGGGGCTACATTGCTGGATCCGCTGCGATGGTTGACACCA 2760
 G  K* A  Y  G  C  V  G  G  Y  I  A  G  S  A  A  M  V  D  T
TCCGCTCCCTCGCCCCTGGCTTCATCTTCACCACGTCCTTGCCGCCCGCCACCATGGCTG 2820
 I  R  S  L  A  P  G  F  I  F  T  T  S  L  P  P  A  T  M  A
GTGCAGACACTGCTATCCAGTACCAGGCTCGTCACCAGGGCGACCGCGTCCTGCAGCAGT 2880
 G  A  D  T  A  I  Q  Y  Q  A  R  H  Q  G  D  R  V  L  Q  Q
TGCACACCCGCGCGGTCAAAGCAGCTTTCAAGGAGTTGGATATTCCTGTAATTCCCAACC 2940
 L  H  T  R  A  V  K  A  A  F  K  E  L  D  I  P  V  I  P  N
CCTCCCATATCATTCCGCTCCTGGTTGGGGATGCCGAGGTTGCTAAGAAGGCCTCGGACA 3000
 P  S  H  I  I  P  L  L  V  G  D  A  E  V  A  K  K  A  S  D
AGCTTCTGGAGGAGCATGGAATTTATGTACAAGCCATCAACTACCCAACCGTGCCTCGGG 3060
 K  L  L  E  E  H  G  I  Y  V  Q  A  I  N  Y  P  T  V  P  R
GTGAAGAGCGGCTTCGTATCACGCCCACCCCGGGACATATCAAGGAGCACCGCGACCACC 3120
 G  E  E  R  L  R  I  T  P  T  P  G  H  I  K  E  H  R  D  H
TGGTGCAAGCCGTCCAAACAGTCTGGAACGAACTGGGCATCAAACGCACCAGCGATTGGG 3180
 L  V  Q  A  V  Q  T  V  W  N  E  L  G  I  K  R  T  S  D  W
AAGCGCAAGGCGGCTTCGTCGGCGTGGGTGTCGATGGCGCCGAGGCTGAGAACCAGCCGA 3240
 E  A  Q  G  G  F  V  G  V  G  V  D  G  A  E  A  E  N  Q  P
TTTGGAATGATGTGCAGCTGGGGCTGAAGGAAAACGAAGCCATTGAGGCTGCTGTGGAAC 3300
 I  W  N  D  V  Q  L  G  L  K  E  N  E  A  I  E  A  A  V  E
GCGAGTTTGCCGAGGCCCCCATGCGGACCGCCACCCGTCCTGCCGCGGCTGCTGCTTCGT 3360
 R  E  F  A  E  A  P  M  R  T  A  T  R  P  A  A  A  A  S
CAATCCCGGTGGGTGTGGCTGCCTGAAGTGGCTGCCCGCATGTGAGCTGAAATCGACGTG 3420
 S  I  P  V  G  V  A  A
GAATTCTATACACACACACACACACACACACACACACACACACACACACACACACACACA 3480
CACACACACACACACACACTAACACACACTATGTTATAAATTCCACATCCACTCCTTTGT 3540
CCCTTGTTGGACGTAATTGGTATTTGGACTATTAGTTAGAACCAGTCAGTCGTTACCATG 3600
TGTTTCGGTTCGACTCGAAATCTGACATGTTGTCTGCCCCATGCCACTTCATCTCCTCC 3660
GTAACCGCAGGGCTTCAAATACACTGCCCAGTAATTGTAGTCAATATAGCAGTTAACTAA 3720
CCTTCACCAATTTCCTAATAACAATAGAAGGGGCCATACACGCAGTACCAAAGATCACCT 3780
ACCTCCGATCAATATCCGAACCTCAGGCTACATACATCAAGTCGCATTAATCGATTCCGA 3840
CCTCTGTTTATCCCTGAAAATAACTAAGATCATGATCTACGTTTGGTAAGTGGGACACCT 3900
ACCTACACTGGGAGGTATTGAATAAAGGCATCATTCATATAGTCACAAGATGCCAGGGCC 3960
AATTCATGATATGGATAGCTACTTCCAAACATAATTCAGAGGTATCATTCTGCTCTTCAG 4020
ACAGTTCTTCTCGAAGATCAGTAGGAGCCAGTTTTGACCATTAACTTGTAATGTAATTGC 4080
GATTGTAGTAGATCCGAGATCCATTCACTTTCTAAGGGTTAATTGATTCATTTTACTGAT 4140
ACCTCACCCACCATATT                                            4157
```

FIG. 3B

```
A. oryzae        M E S - - - - L L Q Q S R A M C P F L K R T S P S S L R T L   26
A. nidulans      M E A - - - - L L Q Q S R A M C P F L K R S S P N T L R S L   26
chicken erythroid M A A - - - - F L - - - - - R C P L L A R H P P L A - R A F   20
human erythroid  M V T A A M L L Q - - - - - C C P V L A R G P T S L L G K V   25
mouse erythroid  M V A A A M L L W - - - - - S C P V L S Q G P T G L L G K V   25
chicken hepatic  M E A - - - V V R - - - - - R C P F L A R V S Q A F L Q K A   22
human hepatic    M E S - - - V V R - - - - - R C P F L S R V P Q A F L Q K A   22
rat hepatic      M E T - - - V V R - - - - - R C P F L S R V P Q A F L Q K A   22

A. oryzae        A - - - - - - - T - - - - - A T R P S T S S G G G T M S N L   44
A. nidulans      A - - - - - - - T - - - - - A T R P S T S P G G G T M T N L   44
chicken erythroid A - - - - - - - T - - - - - G A - - - - - - - - - - - - -   24
human erythroid  V K T H Q F L F G - - - - - I G - - - - - - - - - - - - -   36
mouse erythroid  A K T Y Q F L F S - - - - - I G - - - - - - - - - - - - -   36
chicken hepatic  G - - - - - - - P S L L F Y A Q - - - - - - - - - - - - -   31
human hepatic    G - - - - - - - K S L L F Y A Q - - - - - - - - - - - - -   31
rat hepatic      G - - - - - - - K S L L F Y A Q - - - - - - - - - - - - -   31

A. oryzae        Q V I A R R C P V M S - - - - - - - - - - - - K A L A V Q S A   63
A. nidulans      Q R I A R R C P V M S - - - - - - - - - - - - K A L A V Q S A   63
chicken erythroid - - - - - R C P F M G - - - - - - - - - - - - F A - H R A A P   37
human erythroid  - - - - - R C P I L A T Q G P N C S Q I H L K A - T K A G G   60
mouse erythroid  - - - - - R C P I L A T Q G P T C S Q I H L K A - T K A G G   60
chicken hepatic  - - - - - H C P K M M - - - - - - - - - - - - E A - A P P A A   44
human hepatic    - - - - - N C P K M M - - - - - - - - - - - - E V - G A K P A   44
rat hepatic      - - - - - N C P K M M - - - - - - - - - - - - E V - G A K P A   44

A. oryzae        - - - - - - - - - - - - - - - - - - R - - M                 65
A. nidulans      - - - - - - - - - - - - - - - - - - R - - M                 65
chicken erythroid - - - - - - - - - - - - - - - - - - E - - L                 39
human erythroid  D S P S W A K G H C P F M L S E - - L Q D G K S K I V Q - K   87
mouse erythroid  - - - - - - - - - - - - - - - E - - L Q D R K S K I V Q - R   72
chicken hepatic  - - - - - - - - - - - - - - - - - - A R G L A T S A S R G Q Q V E   59
human hepatic    - - - - - - - - - - - - - - - - - - P R A L S T A A V H Y Q Q I K   59
rat hepatic      - - - - - - - - - - - - - - - - - - P R T V S T S A A Q C Q Q V K   59

A. oryzae                                                                    65
A. nidulans                                                                  65
chicken erythroid                                                            39
human erythroid  A A P E V Q E D V K A F K T D L P S S L V S V S - - L R - -   113
mouse erythroid  A A P E V Q E D V K T F K T D L L S T M D S T T - - R S - -   98
chicken hepatic  E T P A A Q P E A K K A K E V A Q Q N T D G S Q - - P P - -   85
human hepatic    E T P P A S E K D K T A K A K V Q Q T P D G S Q - - Q S P D   87
rat hepatic      E T P P A N E K E K T A K A A V Q Q A P D E S Q M A Q T P D   89

A. oryzae                                                                    65
A. nidulans                                                                  65
chicken erythroid                                                            39
human erythroid  - - - - - K P F S G P Q E Q E Q I - S G K V T H L I Q N - N M   137
mouse erythroid  - - - - - H S F P S F Q E P E Q T E G A V P H L I Q N - N M   122
chicken hepatic  - - - - - A G H P P A A A V Q S S A T K C P F L A A Q M N H   110
human hepatic    G T Q L P S G H P L P A T S Q G T A S K C P F L A A Q M N Q   117
rat hepatic      G T Q L P P G H P S P S T S Q S S G S K C P F L A A Q L A R   119

A. oryzae                                                                    65
A. nidulans                                                                  65
chicken erythroid                                                            39
human erythroid  P G N Y V F S Y D - - Q F F R                               150
mouse erythroid  T G S Q A F G Y D - - Q F F R                               135
chicken hepatic  K S S N V F C K A - - S L E L                               123
human hepatic    R G S S V F C K A - - S L E L                               130
rat hepatic      R A A A S S A R P V W S F R R                               134
```

FIG. 4

```
A. oryzae      M - - E S L L Q Q S R A M C P F L K R T S P S S L R T L A T   28
A. nidulans    M - - E A L L Q Q S R A M C P F L K R S S P N T L R S L A T   28
human          M V T A A M L L Q - - - C C P V L A R G P T S L L G K V V K   27
S. cerevisae   M - - Q - - - - - - - - - - - - - - - - - - - R S I F A       7

A. oryzae      A T R P S T S S G G G T M S N L Q V I A R R C P V M S - K A   57
A. nidulans    A T R P S T S P G G G T M T N L Q R I A R R C P V M S - K A   57
human          T H Q F L F G I G - - - - - - - - - - - - R C P I L A T Q G   45
S. cerevisae   - - - - - - - - - - - - - - - - - - - - - - - - - - - -       7

A. oryzae      L A V Q S A R M A G T K R F T S C A A G I T G L G N - - - K   84
A. nidulans    L A V Q S A R M T G T K R F T S S A A G V P G A G T P K       87
human          P N C S Q I H L K A T K A G G D S P S W A K G H C P F M L S   75
S. cerevisae   - - - - - - - - - - - R F G N S S A A V S T L N R L S T T    25

A. oryzae      H C R A P T G K R T L H S T S G N G A N V S A E I Y K N T Q  114
A. nidulans    P T R G S P G K R A L H S T G G N G A N M S T E F H K G A Q  117
human          E L Q D G K S K - I V Q K A A P E V Q E D V K A F K T D L P  104
S. cerevisae   A - - A P H A K N G Y A T A T G A G A A A T A - - - - - -   47

A. oryzae      R D P A G F S K I K T P A N A T A A A A T S G P R P E - - -  141
A. nidulans    Q I H P G L S N A - T R S H V G A S A T V S G P T P R - - -  143
human          S S L V S V S L R K P F S G P Q E Q E Q I S G K V T H L I Q  134
S. cerevisae   - - - - - - - - - - - T A S S T H A A A A A A A A N H - - -  64

A. oryzae      - - A P V A K P F N Y N S F Y N T E L E K K H K D K S Y R Y  169
A. nidulans    - - A P V A A P F D Y D A F Y N A E L Q K K H Q D K S Y R Y  171
human          N N M P G N Y V F S Y D Q F F R D K I M E K K Q D H T Y R V  164
S. cerevisae   - - S T Q E S G F D Y E G L I D S E L Q K K R L D K S Y R Y   92

A. oryzae      F N N I N R L A Q E F P R A H T - - - - T S A E E R V T V W  195
A. nidulans    F N N I N R L A Q E F P R A H T - - - - A S K D E K V T V W  197
human          F K T V N R W A D A Y P F A Q H F F E A S V A S K D V S V W  194
S. cerevisae   F N N I N R L A K E F P L A H R - - - - Q R E A D K V T V W  118

A. oryzae      C S N D Y L G M G R N P E V L A T M H K T L D T Y G A G A G  225
A. nidulans    C S N D Y L G M G R N P E V L A T M H K T L D T Y G A G A G  227
human          C S N D Y L G M S R H P Q V L Q A T Q E T L Q R H G A G A G  224
S. cerevisae   C S N D Y L A L S K H P E V L D A M H K T I D K Y G C G A G  148

A. oryzae      G T R N I S G H N Q H A V S L E N T L A K L H G K E A A L V  255
A. nidulans    G T R N I S G H N Q H A V S L E N T L A K L H G K E A A L V  257
human          G T R N I S G T S K F H V E L E Q E L A E L H Q K D S A L L  254
S. cerevisae   G T R N I A G H N I P T L N L E A E L A T L H K K E G A L V  178
```

FIG. 5A

```
A. oryzae     FSSCFVANDATLATLGSKLPDCVILSDSLN 285
A. nidulans   FSSCFVANDATLATLGSKMPDCVILSDSLN 287
human         FSSCFVANDSTLFTLAKILPGCEIYSDAGN 284
S. cerevisae  FSSCYVANDAVLSLLGQKMKDLVIFSDELN 208

A. oryzae     HASMIQGIRHSGAKKMVFKHNDLVDLEAKL 315
A. nidulans   HASMIQGIRHSGRKKMVFKHNDLVDLETKL 317
human         HASMIQGIRNSGAAKFVFRHNDPDHLKKLL 314
S. cerevisae  HASMIVGIKHANVKKHIFKHNDLNELEQLL 238

A. oryzae     AALPLHVPKIIAFESVYSMCGSIAPIEKIC 345
A. nidulans   ASLPLHVPKIIAFESVYSMCGSIAPIEAIC 347
human         EKSNPKIPKIVAFETVHSMDGAICPLEELC 344
S. cerevisae  QSYPKSVPKLIAFESVYSMAGSVADIEKIC 268

A. oryzae     DLADKYGAITFLDEVHAVGMYGPHGAGVAE 375
A. nidulans   DLADKYGAITFLDEVHAVGMYGPHGAGVAE 377
human         DVSHQYGALTFVDEVHAVGLYGSRGAGIGE 374
S. cerevisae  DLADKYGALTFLDEVHAVGLYGPHGAGVAE 298

A. oryzae     HLDYDIYASQDTVNPRST-KG---TVMDRI 401
A. nidulans   HLDYEIYASQDTANPLST-KG---TVMDRI 403
human         R---------------------DGIMHKI 382
S. cerevisae  HCDFESHRASGIATPKTNDKGGAKTVMDRV 328

A. oryzae     DIITGTLGKAYGCVGGYIAGSAAMVDTIRS 431
A. nidulans   NIITGTLGKAYGCVGGYIAGSAALVDTIRS 433
human         DIISGTLGKAFGCVGGYIASTRDLVDMVRS 412
S. cerevisae  DMITGTLGKSFGSVGGYVAASRKLIDWFRS 358

A. oryzae     LAPGFIFTTSLPPATMAGADTAIQYQARHQ 461
A. nidulans   LAPGFIFTTSLPPATMAGADTAIRYQARHQ 463
human         YAAGFIFTTSLPPMVLSGALESVRLLKGEE 442
S. cerevisae  FAPGFIFTTTLPPSVMAGATAAIRYQRCHI 388
```

FIG. 5B

```
A. oryzae      GD--RVLQQLHTRAVKAAFKELDIPVIPNP  489
A. nidulans    QD--RILQQLHTRAVKQSFKDLDIPVIPNP  491
human          GQALRRAHQRNVKHMRQLLMDRGLPVIPCP   472
S. cerevisae   DL--RTSQQKHTMYVKKAFHELGIPVIPNP  416

A. oryzae      SHIIPLLVGDAEVAKKASDKLLEEHGIYVQ  519
A. nidulans    SHIVPLLVGDAELAKQASDKLLEEHGIYVQ  521
human          SHIIPIRVGNAALNSKLCDLLLSKHGIYVQ   502
S. cerevisae   SHIVPVLIGNADLAKQASDILINKHQIYVQ  446

A. oryzae      AINYPTVPRGEERLRITPTPGHIKEHRDHL  549
A. nidulans    AINYPTVPRGEERLRITPTPGHTQELRDHL  551
human          AINYPTVPRGEELLRLAPSPHHSPQMMEDF   532
S. cerevisae   AINFPTVARGTERLRITPTPGHTNDLSDIL  476

A. oryzae      VQAVQTVWNELGIKRTSDWEAQGGFVGVGV  579
A. nidulans    VEAVNTVWNDLGIKRASDWKAMGGFVGVGV  581
human          VEKLLLAWTAVGLP-----------LQDVSV  552
S. cerevisae   INAVDDVFNELQLPRVRDWESQGGLLGVG-  505

A. oryzae      DGAEAENQPIWNDVQLGLKENEAIEAAVER  609
A. nidulans    EAAELENQPIWTDQLNMRPDETLEAAVER   611
human          AACNFCRRPV----HFELMSE------WER  572
S. cerevisae   ESGFVEESNLWTSSQLSLTNDDLN------  529

A. oryzae      EFAEA----------PMRTATRPAAAAASS  629
A. nidulans    EFQAAVPGMKAGGAKAKPVGSIAANPIGAS  641
human          SYFGNM-------------------G      579
S. cerevisae   -------PNVRDPIVKQLEVSS--------  544

A. oryzae      IPVGVA-A    636
A. nidulans    IPVAAAAZ    649
human          PQYVTTYA    587
S. cerevisae   ----GIKQ    548
```

FIG. 5C

ASPERGILLUS ORYZAE 5-AMINOLEVULINIC ACID SYNTHASES AND NUCLEIC ACIDS ENCODING SAME

CROSS-REFERENCE TO RELATED APPLICATIONS

This application is a divisional of application Ser. No. 08/871,266 filed Jun. 9, 1997 which is a continuation-in-part of application Ser. No. 60/019,399 filed Jun. 10, 1996, the contents of which are fully incorporated herein by reference.

BACKGROUND OF THE INVENTION

1. Field of the Invention

The present invention relates to *Aspergillus oryzae* 5-aminolevulinic acid synthases and isolated nucleic acid fragments comprising nucleic acid sequences encoding the 5-aminolevulinic acid syntheses. The invention also relates to nucleic acid constructs, vectors, and host cells comprising the nucleic acid sequences as well as methods for producing the 5-aminolevulinic acid synthases.

2. Description of the Related Art

Heme, a chelate complex of protoporphyrin IX and iron, serves as a prosthetic group of hemoproteins. Protoporphyrin IX consists of a porphyrin ring, substituted with four methyl groups, two vinyl groups, and two propionic acid groups, which acquires an iron atom to form heme. The biosynthesis of heme from glycine and succinyl-CoA involves eight enzymatic steps. The first enzyme in the biosynthetic pathway is 5-aminolevulinic acid synthase which catalyzes the condensation of glycine and succinyl-CoA to form 5-aminolevulinic acid. In the biosynthesis of heme in liver cells and differentiating erythrocytes, 5-aminolevulinic acid synthase is a key regulatory enzyme.

The conversion of an apoprotein into a hemoprotein depends on the availability of heme provided by the heme biosynthetic pathway. The apoprotein form of the hemoprotein combines with heme to produce the active hemoprotein. The active hemoprotein acquires a conformation which makes the hemoprotein more stable than the apoprotein to proteolytic attack. If the amount of heme produced by a microorganism is less relative to the amount of the apoprotein produced, the apoprotein will accumulate and undergo proteolytic degradation lowering the yield of the active hemoprotein.

In order to overcome this problem, Jensen showed that the addition of heme or a heme-containing material to a fermentation medium led to a significant increase in the yield of a peroxidase produced by *Aspergillus oryzae* (WO 93/19195). While heme supplementation of a fermentation medium results in a significant improvement in the yield of a hemoprotein, it is non-kosher, costly, and difficult to implement on a large scale.

The cloning and sequencing of a 5-aminolevulinic acid synthase gene from *Aspergillus nidulans* (Bradshaw et al., 1993, *Current Genetics* 2233:501–507) have been disclosed.

It is an object of the present invention to provide new 5-aminolevulinic acid synthases and genes encoding same.

SUMMARY OF THE INVENTION

The present invention relates to substantially pure 5-aminolevulinic acid synthases obtained from *Aspergillus oryzae* and to isolated nucleic acid fragments comprising a nucleic acid sequence which encodes an *Aspergillus oryzae* 5-aminolevulinic acid synthase. The present invention further provides nucleic acid constructs, vectors, and recombinant host cells comprising a nucleic acid fragment of the present invention as well as methods for producing the 5-aminolevulinic acid synthases.

BRIEF DESCRIPTION OF THE FIGURES

FIGS. 3A–3B shows the nucleotide and deduced amino acid sequences of an *Aspergillus oryzae* 5-aminolevulinic acid synthase gene (SEQ ID NOS: 1 and 2, respectively). Potentially important transcriptional sites, CCAAT box and TATA box are underlined. The two conserved putative HRM motifs are boxed; the glycine loop involved in pyridoxal phosphate co-factor binding is circled and the important lysine is indicated with an asterisk.

FIG. 4 shows the conserved heme regulatory motifs in various 5-aminolevulinic acid synthase genes. The pentapeptide motifs are boxed.

FIGS. 5A–5C shows the alignment of the deduced amino acid sequences for 5-aminolevulinic acid synthases from *Aspergillus oryzae, Aspergillus nidulans, Saccharomyces cerevisiae* and human erythroid (SEQ ID NOS:2, 16, 17 and 18, respectively). Conserved amino acids are boxed.

DETAILED DESCRIPTION OF THE INVENTION

Figure 1:
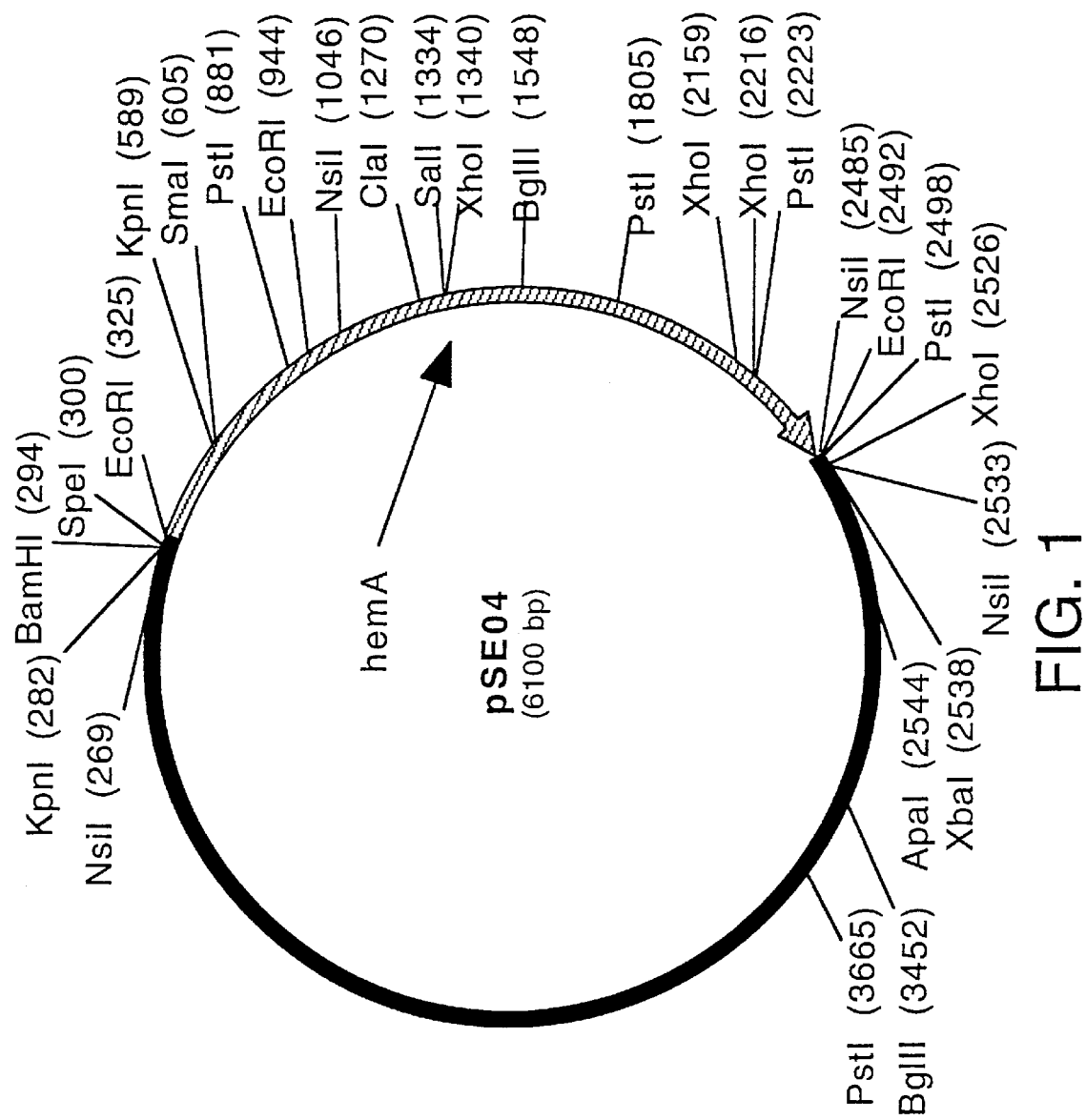
FIG. 1 shows a restriction map of plasmid pSE04.

The present invention, as mentioned above, relates to 5-aminolevulinic acid synthases obtained from an *Aspergillus oryzae* strain. Strains of this species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), International Mycological Institute (IMI), Agricultural Research Service Patent Culture Collection, Northern Regional Research Center (NRRL), and Institute for Fermentation in Osaka, Japan (IFO).

In a preferred embodiment, the present invention relates to 5-aminolevulinic acid synthases obtained from *Aspergillus oryzae* or a mutant strain thereof. In a more preferred embodiment, the present invention relates to 5-aminolevulinic acid synthases obtained from *Aspergillus oryzae* IFO 4177 or a mutant strain thereof, e.g., the 5-aminolevulinic acid synthase having the amino acid sequence set forth in SEQ ID NO:2.

The present invention also relates to 5-aminolevulinic acid synthases which are encoded by nucleic acid sequences which are capable of hybridizing under high stringency conditions (i.e., prehybridization and hybridization at 45° C. in 5 X SSPE, 0.3% SDS, 200 µg/ml sheared and denatured salmon sperm DNA, and 50% formamide) with a probe which hybridizes with the nucleic acid sequence set forth in SEQ ID NO:1 under the same conditions. The gene, or an oligonucleotide based thereon, can be used as a probe in Southern hybridization to isolate homologous genes of any Aspergillus species. In particular, such probes can be used for hybridization with the genomic or cDNA of the species of interest, following standard Southern blotting procedures, in order to identify and isolate the corresponding 5-aminolevulinic acid synthase gene therein. Degenerate PCR primers (oligonucleotides) can be used with genomic DNA or cDNA segments to amplify 5-aminolevulinic acid synthase-specific gene segments.

Identification and isolation of 5-aminolevulinic acid synthase genes from a source other than those specifically exemplified herein can be achieved by utilization of the methodology described in the present examples, with publicly available Aspergillus strains.

For purposes of the present invention, the term "obtained from" means that the 5-aminolevulinic acid synthase is produced by a specific source, e.g., an Aspergillus strain, or by a cell in which a gene from the source encoding the 5-aminolevulinic acid synthase has been inserted.

The invention also encompasses 5-aminolevulinic acid synthase variants which have at least about 80%, preferably about 85%, more preferably about 90%, and most preferably about 95% homology with the amino acid sequence set forth in SEQ ID NO:2, and which qualitatively retains the activity of the 5-aminolevulinic acid synthases described herein. The present invention is also directed to 5-aminolevulinic acid synthase variants which have an amino acid sequence which differs by three amino acids, preferably by two amino acids, and more preferably by one amino acid from the amino acid sequence set forth in SEQ ID NO:2. Each difference may be an insertion or deletion of an amino acid or the substitution of an amino acid residue by a different amino acid. Useful variants within the categories defined above include, for example, ones in which conservative amino acid substitutions have been made, which substitutions do not significantly affect the activity of the protein. By conservative substitution is meant that amino acids of the same class may be substituted by any other amino acid of that class. For example, the nonpolar aliphatic residues Ala, Val, Leu, and Ile may be interchanged, as may be the basic residues Lys and Arg, or the acidic residues Asp and Glu. Similarly, Ser and Thr are conservative substitutions for each other, as are Asn and Gln.

The physical-chemical properties of the 5-aminolevulinic acid synthases of the present invention may be determined using various techniques well known in the art including, but not limited to, SDS-PAGE, isoelectric focusing, and cross-reaction irmunoidentity tests. The 5-aminolevulinic acid synthases of the present invention may be assayed using methods known in the art.

The 5-aminolevulinic acid synthases of the present invention may be purified by a variety of procedures known in the art including, but not limited to, chromatography (e.g., ion exchange, affinity, hydrophobic, chromatofocusing, and size exclusion), electrophoretic procedures (e.g.., preparative isoelectric focusing), differential solubility (e.g., ammonium sulfate precipitation), or extraction (see, for example, *Protein Purzfication*, eds. J.-C. Janson and Lars Ryden, VCH Publishers, New York, 1989). As defined herein, a "substantially pure" 5-aminolevulinic acid synthase is a 5-aminolevulinic acid synthase which is essentially free of other non-5-aminolevulinic acid synthase proteins, for example, at least about 20% pure, preferably about 40% pure, more preferably about 60% pure, even more preferably about 80% pure, most preferably about 90% pure, and even most preferably at least about 95% pure, as determined by SDS-PAGE.

The present invention also relates to nucleic acid fragments comprising a nucleic acid sequence which encodes a 5-aminolevulinic acid synthase of the present invention and to nucleic acid constructs comprising a nucleic acid fragment of the present invention.

In a preferred embodiment, the nucleic acid sequence encodes a 5-aminolevulinic acid synthase obtained from *Aspergillus oryzae*. In a more preferred embodiment, the nucleic acid sequence encodes a 5-aminolevulinic acid synthase obtained from *Aspergillus oryzae* IFO 4177, e.g., the nucleic acid sequence set forth in SEQ ID NO:1. The present invention also encompasses nucleic acid sequences which encode a 5-aminolevulinic acid synthase having the amino acid sequence set forth in SEQ ID NO:2, which differ from SEQ ID NO:1 by virtue of the degeneracy of the genetic code. The nucleic acid sequences of the present invention encompass both the genomic sequence depicted therein as well as the corresponding cDNA and RNA sequences, and the phrase "nucleic acid sequence" as used herein will be understood to encompass all such variations including synthetic DNA.

The present invention also relates to nucleic acid constructs comprising a nucleic acid fragment of the invention. "Nucleic acid construct" shall generally be understood to mean a nucleic acid molecule, either single- or double-stranded, which is isolated from a naturally occurring gene or which has been modified to contain segments of nucleic acid which are combined and juxtaposed in a manner which would not otherwise exist in nature. In a preferred embodiment, the nucleic acid constructs are operably linked to regulatory regions capable of directing the expression of the 5-aminolevulinic acid synthase in a suitable expression host.

The present invention also provides recombinant vectors comprising a nucleic acid construct of the present invention. In a preferred embodiment, the nucleic acid sequence is operably linked to a promoter sequence. In another preferred embodiment, the vectors of the present invention further comprise a transcription termination signal and/or a selectable marker.

The recombinant vectors of the invention are useful for the expression of an *Aspergillus oryzae* 5-aminolevulinic acid synthase gene in active form. A useful vector contains an element that permits stable integration of the vector into the host cell genome or autonomous replication of the vector in a host cell independent of the genome of the host cell, and preferably one or more phenotypic markers which permit easy selection of transformed host cells. The vector may also include control sequences such as a promoter, ribosome binding site, translation initiation signal, and, optionally, a selectable marker or various activator or repressor sequences. To permit the secretion of the expressed protein, nucleic acids encoding a signal sequence may be inserted prior to the coding sequence of the gene. For expression under the direction of control sequences, a 5-aminolevulinic acid synthase gene to be used according to the present invention is operably linked to the control sequences in such a way that expression of the coding sequence is achieved under conditions compatible with the control sequences.

The vectors carrying a nucleic acid construct of the present invention may be any vector which can conveniently be subjected to recombinant DNA procedures. The choice of a vector will typically depend on the host cell into which the vector is to be introduced. The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. Alternatively, the vector may be one which, when introduced into a host cell, is integrated into the host cell genome and replicated together with the chromosome(s) into which it has been integrated. The vector system may be a single vector or plasmid or two or more vectors or plasmids which together contain the total DNA to be integrated into the genome.

In the vectors, the DNA sequence should be operably linked to a suitable promoter sequence. The promoter may be any DNA sequence which shows transcriptional activity in the host cell of choice and may be obtained from genes encoding proteins either homologous or heterologous to the host cell. Examples of suitable promoters for directing the transcription of the nucleic acid construct of the invention, especially in a bacterial host, are the promoter of the lac operon of *E. coli,* the *Streptomyces coelicolor* agarase gene dagA promoters, the promoters of the *Bacillus licheniformis* α-amylase gene (amyL), the promoters of the *Bacillus stearothermophilus* maltogenic amylase gene (amyM), the promoters of the *Bacillus amyloliquefaciens* α-amylase (amyQ), the promoters of the *Bacillus subtilis* xylA and xylB genes, the prokaryotic β-lactamase promoter (Villa-Kamaroff et al., 1978, *Proceedings of the National Academy of Sciences U.S.A.* 75:3727–3731) or the tac promoter (DeBoer et al., 1983, *Proceedings of the National Academy of Sciences U.S.A.* 80:21–25). Further promoters are described in "Useful proteins from recombinant bacteria" in *Scientific American,* 1980, 242:74–94; and in Sambrook et al., *Molecular Cloning, A Laboratory Manual,* 2d ed., Cold Spring Harbor, N.Y., 1989. In a yeast host, a useful promoter is the eno-1 promoter. For transcription in a fungal host, examples of useful promoters are those obtained from the genes encoding *Aspergillus oryzae* TAKA amylase, *Rhizomucor miehei* aspartic proteinase, *Aspergillus niger* neutral α-amylase, *Aspergillus niger* acid stable α-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase or *Aspergillus nidulans* acetamidase. Particularly preferred promoters are the TAKA amylase, NA2-tpi (a hybrid of the promoters from the genes encoding *Aspergillus niger* neutral α-amylase and *Aspergillus oryzae* triose phosphate isomerase), and glaA promoters.

The vectors of the invention may also comprise a suitable transcription terminator and, in eukaryotes, polyadenylation sequences operably connected to the DNA sequence encoding a 5-aminolevulinic acid synthase of the present invention. Termination and polyadenylation sequences may be obtained from the same sources as the promoter. The vectors may further comprise a DNA sequence enabling the vectors to replicate in the host cell in question. Examples of such sequences are the origins of replication of plasmids pUC19, pACYC177, pUB110, pE194, pAMB1, and pIJ702.

The vectors of the present invention preferably contain one or more selectable markers which permit easy selection of transformed cells. A selectable marker is a gene the product of which provides for biocide or viral resistance, resistance to heavy metals, prototrophy to auxotrophs and the like. The selectable marker may be selected from the group consisting of, but not limited to, amdS, pyrG, argB, niaD, sC, trpC, bar, and hygB. Preferred for use in an Aspergillus cell are the amdS and pyrG markers of *Aspergillus nidulans* or *Aspergillus oryzae* and the bar marker of *Streptomyces hygroscopicus.* Furthermore, selection may be accomplished by co-transformation, e.g., as described in WO 91/17243 where the selectable marker is contained in a separate vector.

The vectors of the invention preferably also contain a signal peptide coding region, which codes for an amino acid sequence linked to the amino terminus of the heme biosynthetic enzyme, permitting the localization of the 5-aminolevulinic acid synthase to a particular cellular compartment. The signal peptide coding region may be native to the first nucleic acid sequence encoding the 5-aminolevulinic acid synthase or may be obtained from foreign sources. The 5' end of the coding sequence of the first nucleic acid sequence may inherently contain a signal peptide coding region naturally linked in translation reading frame with the segment of the coding region which encodes the localized 5-aminolevulinic acid synthase. Alternatively, the 5' end of the coding sequence may contain nucleic acids encoding a signal peptide coding region which is foreign to that portion of the coding sequence which encodes the localized heme biosynthetic enzyme. The signal peptide coding region may be obtained from a *Neurospora crassa* ATPase gene (Viebrock et al., 1982, *EMBO Journal* 1:565–571) or from a *Saccharomyces cerevisiae* cytochrome c peroxidase gene (Kaput et al., 1982, *Journal of Biological Chemistry* 257:15054–15058). However, any signal peptide coding region capable of permitting localization of the 5-aminolevulinic acid synthase in a filamentous fungal host of choice may be used in the present invention.

To avoid the necessity of disrupting the cell to obtain the expressed 5-aminolevulinic acid synthase, and to minimize the amount of possible degradation of the expressed 5-aminolevulinic acid synthase within the cell, it is preferred that expression of the 5-aminolevulinic acid synthase gene gives rise to a product secreted outside the cell. To this end, the 5-aminolevulinic acid synthases of the present invention may thus comprise a preregion permitting secretion of the expressed protein into the culture medium. If desirable, this preregion may be native to the 5-aminolevulinic acid synthase of the invention or substituted with a different preregion or signal sequence, conveniently accomplished by substitution of the DNA sequences encoding the respective preregions. For example, the preregion may be obtained from a glucoamylase or an amylase gene from an Aspergillus species, an amylase gene from a Bacillus species, a lipase or proteinase gene from *Rhizomucor miehei,* the gene for the α-factor from *Saccharomyces cerevisiae* or the calf prepro-chymosin gene. Particularly preferred is the preregion for *Aspergillus oryzae* TAKA amylase, *Aspergillus niger* neutral amylase, the maltogenic amylase from Bacillus NCIB 11837, *Bacillus stearothermophilus* α-amylase, or *Bacillus licheniformis* subtilisin. An effective signal sequence for fungal hosts is the *Aspergillus oryzae* TAKA amylase signal, the *Rhizomucor miehei* aspartic proteinase signal, or the *Rhizomucor miehei* lipase signal.

The procedures used to ligate the nucleic acid construct of the invention, the promoter, terminator and other elements, and to insert them into suitable vectors containing the information necessary for replication, are well known to persons of ordinary skill in the art (cf., for instance, Sambrook et al., supra).

The present invention also relates to host cells comprising a nucleic acid construct or an expression vector of the invention which are advantageously used in the recombinant production of the 5-aminolevulinic acid synthases of the invention. The cell may be transformed with the nucleic acid construct of the invention, conveniently by integrating the construct into the host chromosome. This integration is generally considered to be an advantage as the sequence is more likely to be stably maintained in the cell. Integration of the construct into the host chromosome may be performed according to conventional methods, e.g., by homologous or non-homologous recombination. Alternatively, the cell may be transformed with an expression vector as described below in connection with the different types of host cells.

The choice of host cells and vectors will to a large extent depend upon the 5-aminolevulinic acid synthase and its source. The host cell may be selected from prokaryotic cells, such as bacterial cells. Examples of suitable bacteria are gram-positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis,* or *Streptomyces lividans* or *Streptomyces murinus,* or gram-negative bacteria such as *E. coli.* The transformation of the bacteria may, for instance, be effected by protoplast transformation or by using competent cells in a manner known per se.

The host cell is preferably a eukaryote, such as a mammalian cell, an insect cell, a plant cell or preferably a fungal cell, including yeast and filamentous fungi. For example, useful mammalian cells include CHO or COS cells. A yeast host cell may be selected from a species of Saccharomyces or Schizosaccharomyces, e.g., *Saccharomyces cerevisiae.* Useful filamentous fungi may be selected from a species of Aspergillus, e.g., *Aspergillus oryzae* or *Aspergillus niger.* Alternatively, a strain of a Fusarium species, e.g., *Fusarium oxysporum* or *Fusarium graminearum,* can be used as a host cell. Fungal cells may be transformed by a process involving protoplast formation, transformation of the protoplasts, and regeneration of the cell wall in a manner known per se. A suitable procedure for transformation of Aspergillus host cells is described in EP 238 023. A suitable method of transforming Fusarium species is described by Malardier et al, 1989, *Gene* 78:147–156 or in copending U.S. Ser. No. 08/269,449.

In a particularly preferred embodiment, the expression of the 5-aminolevulinic acid synthase gene is achieved in a fungal host cell, such as Aspergillus. The 5-aminolevulinic acid synthase gene is ligated into a plasmid preferably containing the *Aspergillus oryzae* TAKA amylase promoter or the *Aspergillus niger* neutral amylase NA2 promoter and amdS or pyrG as the selectable marker. Alternatively, the selectable marker may be on a separate plasmid and used in co-transformation. The plasmid (or plasmids) is used to transform an Aspergillus species host cell, such as *Aspergillus oryzae* or *Aspergillus niger* in accordance with methods described in Yelton et al., 1984, *Proceedings of the National Academy of Sciences U.S.A.* 81:1470–1474.

The present invention also relates to methods for producing a 5-aminolevulinic acid synthase of the present invention comprising (a) cultivating an *Aspergillus oryzae* strain in a nutrient medium to produce the 5-aminolevulinic acid synthase, and (b) recovering the 5-aminolevulinic acid synthase.

The present invention also relates to methods for recombinantly producing a 5-aminolevulinic acid synthase of the present invention comprising (a) fermenting a host cell comprising a nucleic acid construct comprising a nucleic acid sequence encoding the 5-aminolevulinic acid synthase under conditions conducive to the production of the enzyme, and (b) recovering the 5-aminolevulinic acid synthase. If the expression system secretes the 5-aminolevulinic acid synthase into the fermentation medium, the enzyme can be recovered directly from the medium. If the recombinant 5-aminolevulinic acid synthase is not secreted, it is recovered from cell lysates.

Any method of cultivation of a cell known in the art may be used which results in the expression or isolation of a 5-aminolevulinic acid synthetase of the present invention. For example, cultivation may be understood as comprising shake flask cultivation, small- or large-scale fermentation (including continuous, batch, fed-batch, or solid state fermentations) in laboratory or industrial fermentors performed in a suitable medium and under conditions allowing the 5-aminolevulinic acid synthase to be expressed or isolated. The cultivation takes place in a suitable nutrient medium comprising carbon and nitrogen sources and inorganic salts using procedures known in the art (see, e.g., Bennett, J. W. and LaSure, L. (eds.), *More Gene Manipulations in Fungi,* Academic Press, California, 1991). Suitable media are available from commercial suppliers or may be prepared according to published compositions (e.g., in catalogues of the American Type Culture Collection).

The 5-aminolevulinic acid synthases produced by the methods described above may be recovered from the fermentation medium by conventional procedures including, but not limited to, centrifugation, filtration, spray-drying, evaporation, or precipitation. The recovered protein may then be further purified by a variety of chromatographic procedures, e.g., ion exchange chromatography, gel filtration chromatography, affinity chromatography, or the like.

The present invention is also directed to methods of using the 5-amininolevulinic acid synthases.

The 5-aminolevulinic acid synthases of the present invention may be used to convert glycine and succinyl-CoA to 5-aminolevulinic acid which is useful as a herbicide.

The 5-aminolevulinic acid synthases of the present invention may be also used to increase the yield of a hemoprotein produced by a host cell, where 5-aminolevulinic acid synthase is a rate-limiting step in the production of heme in the host cell, by overexpressing the nucleic acid sequence encoding the 5-aminolevulinic acid synthase in the host cell. The method comprises:

(a) introducing into the host cell, which is capable of producing the hemoprotein, one or more copies of the nucleic acid sequence encoding the 5-aminolevulinic acid synthase, wherein the nucleic acid sequence is operably linked to regulatory regions capable of directing the expression of the 5-aminolevulinic acid synthase;

(b) cultivating the cell in a nutrient medium suitable for production of the hemoprotein and the 5-aminolevulinic acid synthase; and (c) recovering the hemoprotein from the nutrient medium of the cell.

The present invention is further described by the following examples which should not be construed as limiting the scope of the invention.

EXAMPLES

Example 1

*Aspergillus oryzae* Strain A1560 Genomic DNA Extraction

*Aspergillus oryzae* strain A1560 (IFO 4177) was grown in 25 ml of 0.5% yeast extract-2% glucose (YEG) medium for 24 hours at 32° C. and 250 rpm. Mycelia were then collected by filtration through Miracloth (Calbiochem, La Jolla, Calif.) and washed once with 25 ml of 10 mM Tris-1 mM EDTA (TE) buffer. Excess buffer was drained from the mycelia which were subsequently frozen in liquid nitrogen. The frozen mycelia were ground to a fine powder in an electric coffee grinder, and the powder was added to 20 ml of TE buffer and 5 ml of 20% w/v sodium dodecylsulfate (SDS) in a disposable plastic centrifuge tube. The mixture was gently inverted several times to insure mixing, and extracted twice with an equal volume of phenol:chloroform:isoamyl alcohol (25:24:1 v/v/v). Sodium acetate (3 M solution) was added to a fmal concentration of 0.3 M followed by addition of 2.5 volumes of ice cold ethanol to precipitate the nucleic acids. The nucleic acids were then pelleted by centrifuging the tube at 15,000×g for 30 minutes. The pellet was allowed to air dry for 30 minutes before resuspension in 0.5 ml of TE buffer. DNase-free ribonuclease A was added to a concentration of 100 µg/ml and the mixture was incubated at 37ûC. for 30 minutes. Proteinase K was then added at a concentration of 200 µg/ml and the mixture was incubated an additional hour at 37° C. Finally, the mixture was extracted twice with phenol:chloroform:isoamyl alcohol (25:24:1 v/v/v) before precipitating the DNA with sodium acetate and ethanol as described earlier. The DNA pellet was dried under vacuum, resuspended in TE buffer, and stored at 4° C. until further use.

Example 2

Construction of Plasmid pSE04

Genomic DNA was obtained from *Aspergillus nidulans* strain A26 (Fungal Genetics Stock Center, Kansas City, Kans.) using the same procedure described in Example 1. Plasmid pSE04 was constructed by ligation of PCR fragments from an amplification reaction containing *Aspergillus nidulans* A26 genomic DNA. The amplification reaction contained the following components: 50 ng of *Aspergillus nidulans* A26 genomic DNA, 100 µM each of dATP, dCTP, dGTP, and dTTP (Boehringer Mannheim, Indianapolis, Ind.), 50 pmoles of primers ALAS3d 5'-TTTATGATGGAGGCCCTTCTCCAGCAGTCTC-3' (SEQ ID NO:3) and ALAS4e 5'-CTATGCATTTAAGCAGCAGCCGCGACTGG-3' (SEQ ID NO:4), 2 units of Taq DNA polymerase (Perkin-Elmer Corp., Branchburg, N.J.), and 1X Taq DNA polymerase buffer (Perkin-Elmer Corp., Branchburg, N.J.). The reaction was incubated in a Perkin-Elmer Thermal Cycler (Perkin-Elmer Corp., Branchburg, N.J.) programmed for 30 cycles each at 95° C. for 1 minute, 55° C. for 1 minute, and 72° C. for 90 seconds. The 2 kb PCR product was isolated by excision after electrophoresis using a 1.1% low melting temperature agarose gel (FMC, Rockland, Me.) with 40 mM Tris-acetate-1 mM disodium EDTA (TAE) buffer, and subcloned into the pCRII vector (Invitrogen, San Diego, Calif.) according to the manufacturer's instructions to produce pSE04 (FIG. 1).

Example 3

*Aspergillus oryzae* Strain A1560 DNA Libraries and Identification of ALA Synthase (hemA) Clones

*Aspergillus oryzae* strain A1560 genomic DNA libraries were constructed using the bacteriophage cloning vector λZipLox (Life Technologies, Gaithersburg, Md.) according to the manufacturer's instructions using *E. coli* Y1090ZL cells as a host for plating and purification of recombinant bacteriophage and *E. coli* DH10Bzip for excision of individual pZL1-hemA clones. Total cellular DNA prepared as described in Example 1 was partially digested with Tsp509I and size-fractionated on a 1% agarose gel with 50 mM Tris-50 mM borate-1 mM disodium EDTA (TBE) buffer. DNA fragments migrating in the size range 4–7 kb were excised and eluted from the gel using Prep-a-Gene reagents (BioRad Laboratories, Hercules, Calif.). The eluted DNA fragments were ligated with EcoRI-cleaved and dephosphorylated λZipLox vector arms, and the ligation mixtures were packaged using commercial packaging extracts (Stratagene, La Jolla, Calif.). The packaged DNA libraries were plated and amplified in *E. coli* Y1090ZL cells. The unamplified genomic library contained $1 \times 10^6$ pfu/ml.

Figure 2:
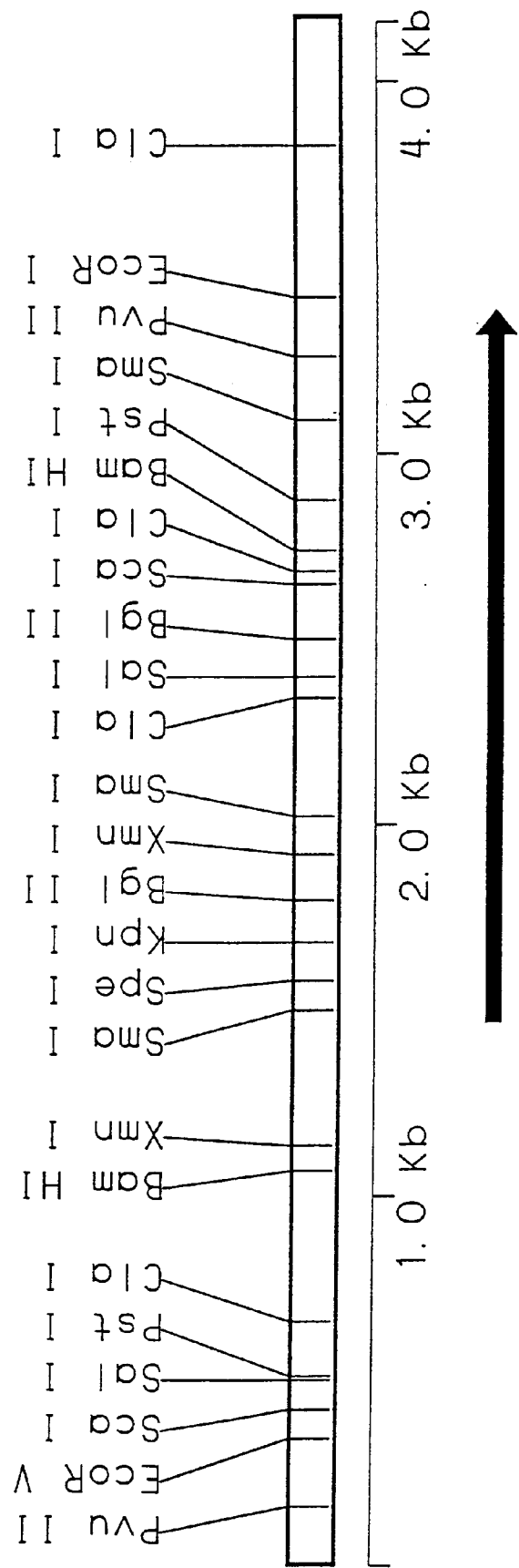
FIG. 2 shows a restriction map of a 4.2 kb genomic fragment containing an *Aspergillus oryzae* 5-aminolevulinic acid synthase gene. Scale in kilobases (kb) is shown under the map. The arrow represents the location of the open reading frame of the gene.

Bacteriophage DNA from $7 \times 10^4$ plaques was transferred to duplicate circular Nytran Plus membranes (Schleicher & Schuell, Keene, N.H.) and probed with a digoxigenin (DIG)-labeled probe which was prepared by PCR amplification of *Aspergillus nidulans* hemA genomic DNA from plasmid pSE04 described in Example 2. The amplification reaction contained the following components: 1X DIG probe synthesis mix (Boehringer Mannheim, Indianapolis, Ind.), 100 µM each of dATP, dCTP, dGTP, and dTTP, 50 pmoles of primer ALAS3d and primer ALAS4e described in Example 2, 2 units of Taq DNA polymerase, and 1X Taq DNA polymerase buffer. The reaction was incubated in a Perkin-Elmer Thermal Cycler programmed for 30 cycles each at 95° C. for 1 minute, 55° C. for 1 minute, and 72° C. for 2 minutes. Denatured probe was added to the hybridization buffer at a concentration of 2 ng/ml and incubated overnight with prehybridized membranes. Prehybridization and hybridization was conducted at 42° C. in 5 X SSC, 0.1% sarkosyl, 0.02% SDS, 1% Genius blocking agent (Boehringer Mannheim, Indianapolis, Ind.), and 30% formamide. Membranes were washed twice in 5 X SSC-0.1% SDS followed by two washes in 2 X SSC-0.1% SDS. Each wash was performed for 15 minutes at room temperature. The washed membrane was exposed to Kodak X-OMAT AR film for approximately 2 hours at room temperature followed by development using a Konica QX-70 automatic film processor according to the manufacturer's instructions. Primary plaques were purified and screened a second time. Five clones were identified and excised into pZL derivatives according to the manufacturer's instructions (Bethesda Research Laboratories, Inc., Gaithersburg, Md.). The pZL derivatives were designated *E. coli* DH5αpSE11, pSE13, pSE15, pSE17, and pSE20. These clones were found to overlap and span a 4.2 kb region for which the restriction map is shown in FIG. 2.

Example 4

Southern Hybridization of *Aspergillus oryzae* Strain A1560 Genomic DNA with a 5-aminolevulinic Acid Synthase (hemA) Probe

*Aspergillus oryzae* strain A1560 genomic DNA (10 µg) prepared as described in Example 1 was restriction digested with either BamHI or EcoRI. The fragments were separated by electrophoresis on a 1% agarose-TBE gel. DNA was transferred to a Nytran Plus membrane in 0.4 N NaOH using a TurboBlot apparatus (Schleicher & Schuell, Keene, N.H.) according to the manufacturer's instructions. The membrane was prehybridized for 2 hours at 42° C. in 5 X SSC, 0.1% sarkosyl, 0.02% SDS, 1% Genius blocking agent (Boehringer Mannheim, Indianapolis, Ind.), and 50% formamide in a Hybaid oven (Labnet, Woodbridge, N.J.). Hybridization was accomplished with a DIG-labeled hemA probe generated by PCR amplification as described in Example 3, except the hemA clone pSE17 was used as a template with primer hemA5' 5'-TCATTT-AAATGATGGAGTCTCTTCTCC-3' (SEQ ID NO:5) and primer hemA3' 5'-TCTTAATTAATCAGCTCACAT-GCGGG-3' (SEQ ID NO:6). DIG-labeled hemA probe (1 ng probe/ml of solution) was added to fresh hybridization buffer and incubated with the membrane overnight at 42° C. Subsequently, the membrane was washed twice for 15 minutes each at room temperature in 5 X SSC-0.1% SDS followed by two washes under the same conditions in 2 X SSC-0.1% SDS. The washed membrane was exposed to Kodak X-OMAT AR film for approximately 2 hours at room temperature followed by development using a Konica QX-70 automatic film processor according to the manufacturer's instructions.

Southern blot hybridization of *Aspergillus oryzae* genomic DNA with the *Aspergillus oryzae* hemA probe showed the presence of hybridization signals consistent with a single gene copy number. A 1.7 kb band observed in the BamHI lane was predicted from the restriction map (FIG. 2).

Example 5

Characterization of *Aspergillus oryzae* A1560 5-aminolevulinic Acid Synthase (hemA) Gene

*E. coli* DH5αpSE17 described in Example 3 was subjected to DNA sequencing according to the following procedure. DNA sequencing was performed with an Applied Biosystems Model 373A Automated DNA Sequencer (Applied Biosystems, Inc., Foster City, Calif.) on both strands using the primer walking technique with dye-terminator chemistry (Giesecke et al., 1992, *Journal of Virol. Methods* 38:47–60) using the M13 reverse (−48) and M13 forward (−20) primers (New England Biolabs, Beverly, Mass.) and primers unique to the DNA being sequenced.

The nucleotide sequence of the cloned gene revealed an open reading frame of 1911 nucleotides as shown in FIG. 3 (SEQ ID NO:1). The coding sequence does not contain any introns which was confirmed by cDNA cloning and sequence analysis which is in contrast to the *Aspergillus nidulans* hemA gene which contains one intron at its 5' end (Bradshaw et al., 1993, *Current Genetics* 23:501–507). The 5' untranslated sequence contains several pyrimidine-rich and AT-rich regions as in other fungal genes (Gurr et al., 1987, In Kinghorn, J. R. (ed.), *Gene Structure in Eukaryotic Microbes*, pp. 93–139, IRL Press, Oxford), a CCAAT sequence at position −249, and a putative TATA box located at position −35. The CCAAT sequence is a consensus binding site for transcriptional regulators which modulate transcription in response to oxygen, such as the Hap2/3/4 transcriptional regulatory complex in yeast and humans (Olesen and Guarente, 1990, *Molecular and Cellular Biology* 12:2302–2314). This regulatory complex is also conserved in mammals, and a CCAAT-binding activity has been identified in *Aspergillus nidulans* (Davis et al., 1993, *Genetica* 90:133–145). The importance of this sequence in the *Aspergillus oryzae* hemA gene is not known and, due to limited sequence information, has not been confirmed in the *Aspergillus nidulans* hemA 5' region (Bradshaw et al., 1993, supra). Transcriptional regulation of the *Aspergillus oryzae* hemA gene in response to oxygen is not currently known, but the *Aspergillus nidulans* hemA gene does not appear to be transcriptionally regulated even under conditions of oxygen limitation (Bradshaw et al., 1993, supra). Interestingly, the yeast HEM1 gene is also constitutively expressed, but its expression is controlled by a balance between positive and negative regulatory sites (Keng and Guarente, 1987, *Proceedings of the National Academy of Sciences U.S.A.* 84:9113–9117). An $(AC)_{35}$ repeat motif occurs in the 3' untranslated region. Similar repeats have also been observed in subtelomeric, intron, and promoter regions of mammalian and yeast genes and have no known function, although they have been implicated in gene amplification events (Passananti et al., 1987, *EMBO Journal* 6:1697–1703).

The deduced amino acid sequence of the *Aspergillus oryzae* strain A1560 gene product is shown in FIG. 3 (SEQ ID NO:2). The nucleotide sequence encodes a predicted protein of 636 amino acids with a molecular weight of 68 kDa. Since this enzyme is located in the mitochondria, the N-terminus is predicted to contain a mitochondrial leader sequence. In fact, the first 35 amino acids are rich in serine, threonine, lysine, and arginine residues consistent with a function as a mitochondrial leader. A potential heme regulatory motif (HRM) occurs in the presumed mitochondrial leader sequences of both the *Aspergillus nidulans* and *Aspergillus oryzae* hemA sequences (FIG. 4). HRMs localized to leader sequences are believed to prevent import of 5-aminolevulinic acid synthase proteins into the mitochondria in mouse via direct interactions with heme (Lathrop and Timko, 1993, *Science* 259:522–525; Zhang and Guarente, 1995, *EMBO Journal* 14:313–320). A second potential HRM also occurs in the beginning of the putative mature protein sequence. It is probable that the HRMs play a role in the regulation of 5-aminolevulinic acid synthase activity. Interestingly, the *Saccharomyces cerevisiae* 5-aminolevulinic acid synthase protein sequence does not contain any putative HRMs and does not appear to be a key regulatory step in yeast heme biosynthesis (Labbe-Bois and Labbe, In Daley, Harry A., ed., *Biosynthesis of Heme and Chlorophylls*, 1990, McGraw Hill Publishers, New York, pp 235–285).

Overall, the deduced amino acid sequence as shown in FIG. 5 shares 81% identity with the *Aspergillus nidulans* hemA gene (SEQ ID NO:16), 57% identity with the *Saccharomyces cerevisiae* HEM1 gene (SEQ ID NO:17; Urban-Grimal, 1986, *European Journal of Biochemistry* 156:511–519), and 51% identity with the human erythroid heml (ALAS2) gene (SEQ ID NO:18; Bishop, 1990, *Nucleic Acids Research* 18:7187–7188) which were determined using the Applied Biosystems GeneAssist program (blosum62.mat matrix). However, the highest degree of conservation occurs in the C-terminal two-thirds of the protein which contains the catalytic domain. Furthermore, the lysine and glycine-loop, important for catalytic activity and pyridoxal phosphate co-factor binding in other 5-aminolevulinic acid synthase enzymes (Ferreira et al., 1995, *Journal of Bioenergetics and Biomembranes* 27:151–159; Ferreira, 1995, *Protein Science* 4:1001–1006) are also highly conserved.

Example 6

Construction of Plasmid pSE31

Figure 6:
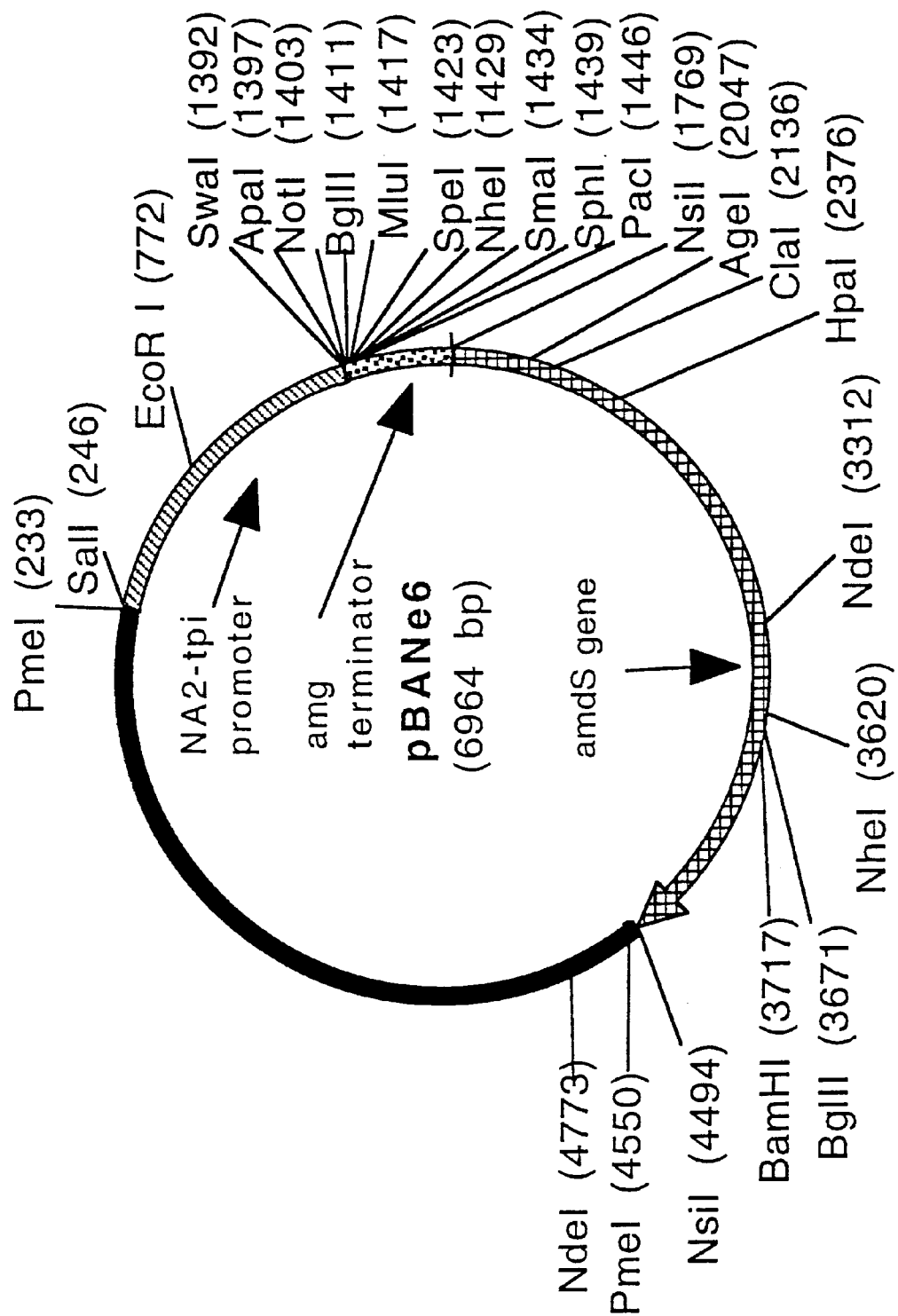
FIG. 6 shows a restriction map of plasmid pBANe6.

Plasmid pSE31 was constructed by directional cloning of PCR-amplified *Aspergillus oryzae* hemA DNA into pBANe6 (FIG. 6). The PCR amplification reaction was performed using DNA from hemA clone *E. coli* DH5α pSE17 described in Example 3 where the reaction contained the following components: 50 ng of pSE17, 2 units of Vent DNA polymerase (New England Biolabs, Beverly, Mass.), 1X Vent DNA polymerase buffer (New England Biolabs, Beverly, Mass.), 400 μM each of dATP, dCTP, dGTP, and dTTP (Boehringer Mannheim, Indianapolis, Ind.), and 50 pmoles of primer hemA5'5'-TC<u>ATTTAAAT</u>GATGGA-GTCTCTTCTCC-3' (SEQ ID NO:5) and primer hemA3'5'-

Figure 7:
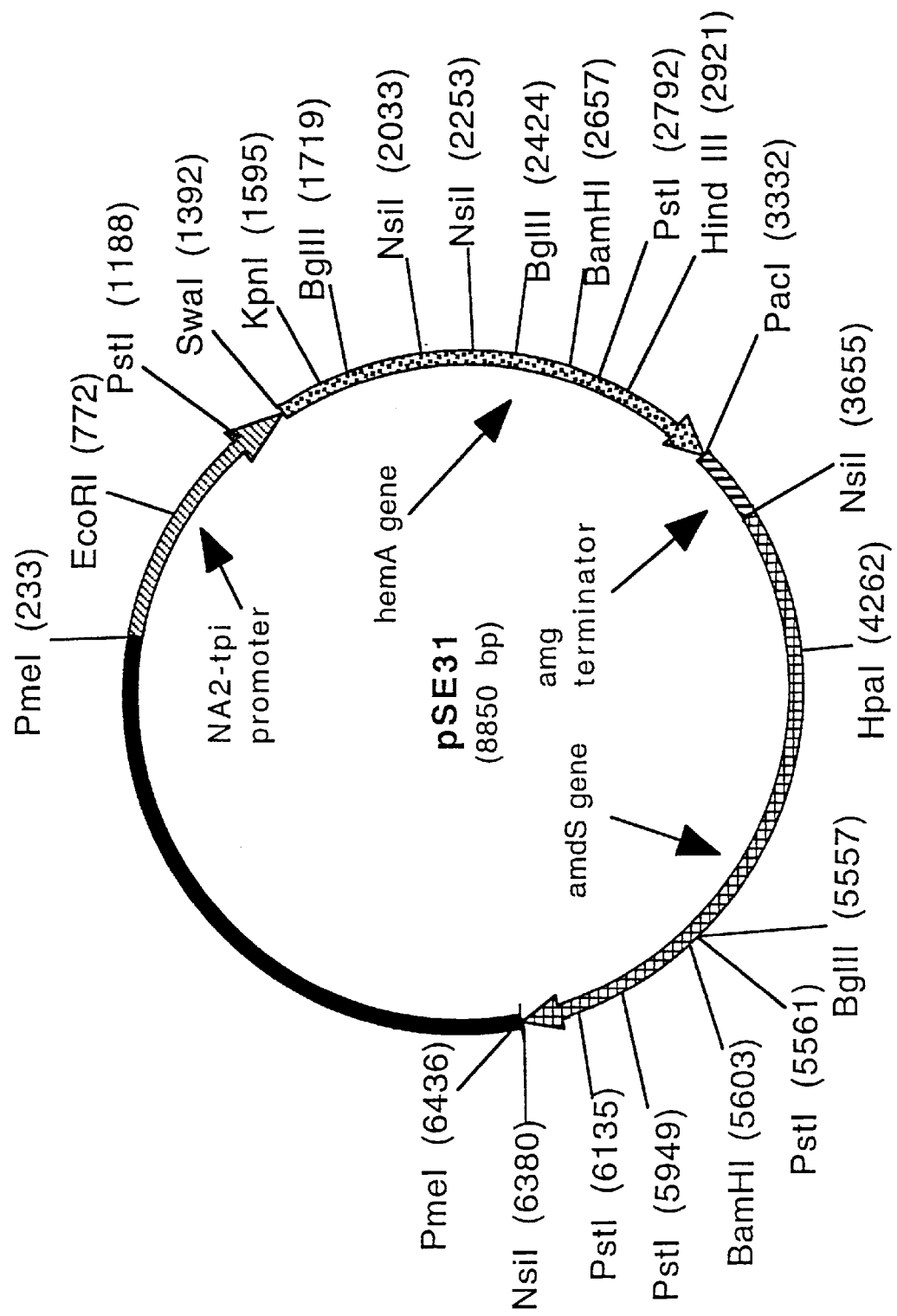
FIG. 7 shows a restriction map of plasmid pSE31.

TC<u>TTAATTAA</u>TCAGCTCACATGCGGG-3' (SEQ ID NO:6). The reaction was incubated in a Perkin-Elmer Thermal Cycler programmed for 30 cycles each at 95° C. for 1 minute, 55° C. for 1 minute, and 72° C. for 90 seconds. Primer hemA5' contains a SwaI site (underlined) and primer hemA3' contains a PacI site (underlined) which were used for cloning into pBANe6 digested with SwaI and PacI to produce pSE31 (FIG. 7).

Example 7

Construction of Aspergillus oryzae Strain JRoC50.3.18A

Aspergillus oryzae strain JRoC50.3.18A containing plasmid pJROC50 was constructed as follows. Coprinus cinereus IFO 8371 peroxidase cDNA fragments were prepared by PCR using specific oligonucleotide primers shown below (Saiki et al., 1988, Science 239:487–491) constructed on the basis of the amino acid sequence of the Coprinus macrorhizus peroxidase (Baunsgaard et al., 1993, European Journal of Biochemistry 213:605–611):

1. 5'-GCGCGAATTCGTNGGNATNGGNATNAA(CT)CA(CT)GG-3' (SEQ ID NO:7)

2. 3'-TACAGNTT(GA)AC(GA)GGNGGCCTAGGCG-5' (SEQ ID NO:8)

3. 5'-GCGAATTCACNCCNCA(GA)GTNTT(CT)GA(CT)AC-3' (SEQ ID NO:9)

4. 3'-GGNAA(GA)GGNCCNCT(CT)AA(GA)CCTAGGCG-5' (SEQ ID NO:10)

5. 5'-GCGCGAATTCTGGCA(GA)TCNAC-3' (SEQ ID NO:11)

6. 5'-GCGCGAATTCTGGCA(GA)AGNATG-3' (SEQ ID NO:12)

7. 3'-CGNTACCGNTT(CT)TACAGCCTAGG-5' (SEQ ID NO:13)

PCR was performed using the Gene Amp Kit and apparatus (Perkin Elmer Cetus, Norwalk, Conn.) in accordance with the manufacturer's instructions with the exception that the reaction was conducted at 28° C. for the first 3 cycles in order to obtain better hybridization to the first strand cDNA (prepared from mRNA obtained from Coprinus cinereus strain IFO 8371) and subsequently at 65° C. for 30 cycles of PCR.

The primers were combined as follows: 1 with 2; 3 with 4; 5 with 7; 6 with 7; 1 with 4; and 3 with 7. The PCR fragments were extended with an EcoRI site at the 5'-end and a BamHI site at the 3'-end. The reactions were analyzed on a 1% agarose-TBE gel where bands of the expected size were found in all the reactions. To verify that the bands corresponded to peroxidase-specific sequences, the gel was subjected to Southern blotting and hybridized to an oligonucleotide probe with the following sequence which is positioned between primers 3 and 4:

5'-GT(CT)TC(GA)AT(GA)TAGAA(CT)TG-3'   (SEQ ID NO:14)

The probe was found to hybridize to bands of approximately 130 bp, 420 bp, 540 bp, and 240 bp, thus confirming that the DNA bands observed corresponded to peroxidase sequences.

DNA from the various PCR reactions was digested with EcoRI and BamHI and cloned into the plasmid pUC19 (New England BioLabs, Beverly, Mass.). Colonies containing the correct PCR fragments were identified by hybridization using the oligonucleotide probe (SEQ ID NO:14) described above. DNA from positive colonies was analyzed by restriction mapping and partial DNA sequence analysis as described by Sanger et al. (1977, Proceedings of the National Academy of Sciences U.S.A. 74:5463–5467). A 430 bp fragment from one of the clones, obtained by using primers 1 and 4, was used to screen a Coprinus cinereus cDNA library as described below.

Figure 8:
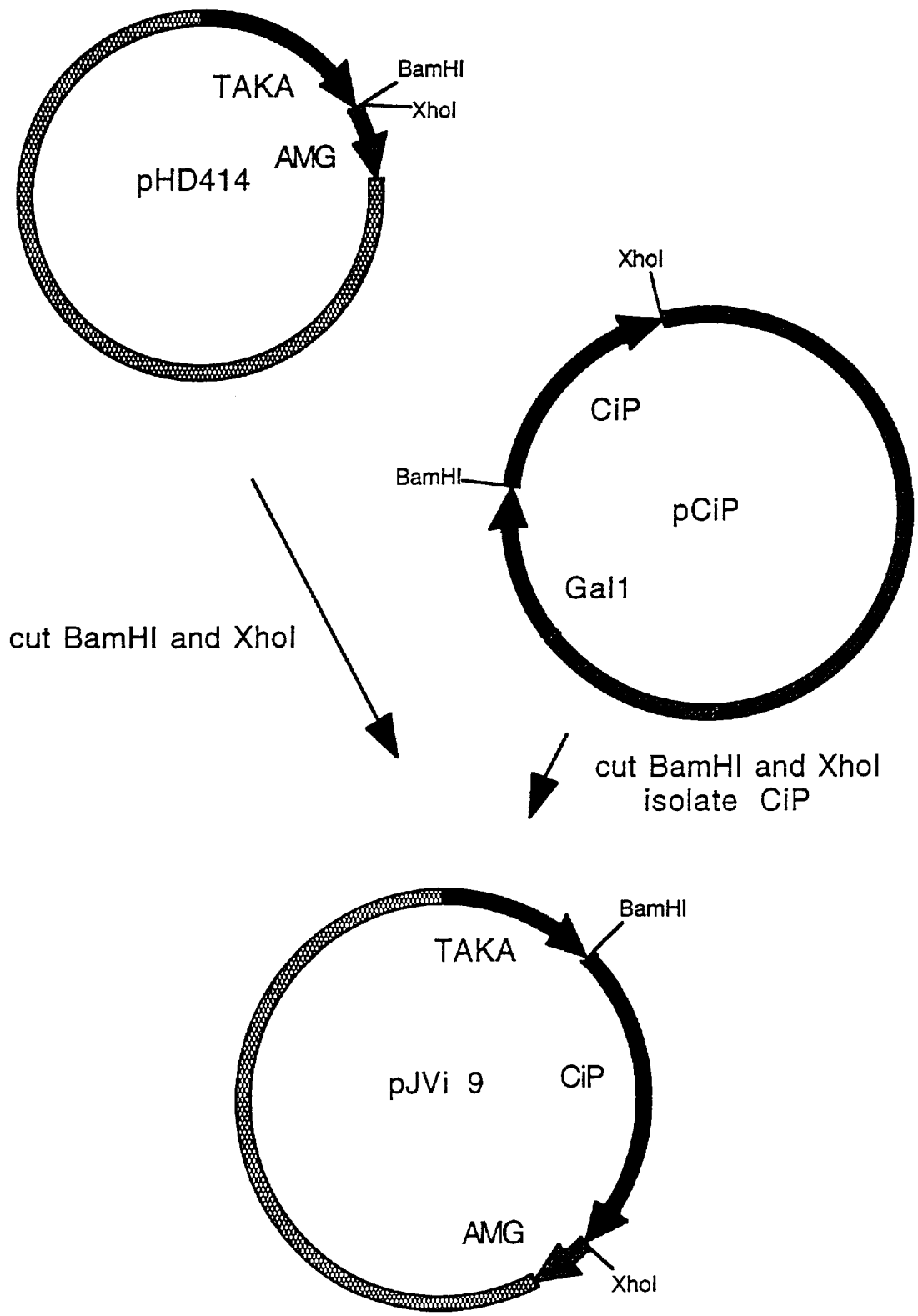
FIG. 8 shows the construction of plasmid pJVi9.

Total RNA was extracted from homogenized Coprinus cinereus strain IFO 8371 mycelia, collected at the time of maximum peroxidase activity according to the methods described by Boel et al. (1984, EMBO Journal 3:1097–1102) and Chirgwin et al. (1979, Biochemistry 18:5294–5299). Poly(A)-containing RNA was obtained by two cycles of affinity chromatography on oligo(dT)-cellulose as described by Aviv and Leder (1972, Proceedings of the National Academy of Sciences U.S.A. 69:1408–1412). cDNA was synthesized by means of a cDNA Synthesis Kit (Invitrogen, San Diego, Calif.) according to the manufacturer's instructions. Approximately 50,000 E. coli recombinants from the Coprinus cinereus cDNA library were transferred to Whatman 540 paper filters. The colonies were lysed and immobilized as described by Gerger et al. (1979, Nucleic Acids Research 7:2115–2135). The filters were hybridized with the $^{32}$P-labelled 430 bp peroxidase-specific probe in 0.2 X SSC-0.1% SDS. Hybridization and washing of the filters was conducted at 65° C. followed by autoradiography for 24 hours with an intensifier screen. After autoradiography, the filters were washed at increasing temperatures followed by autoradiography for 24 hours with an intensifier screen. In this way, more than 50 positive clones were identified. Miniprep plasmid DNA was isolated from hybridizing colonies by standard procedures (Birnboim and Doly, 1979, Nucleic Acids Research 7:1513–1523), and the DNA sequences of the cDNA inserts were determined by the Sanger dideoxy procedure (Sanger et al., 1977, Proceedings of the National Academy of Sciences U.S.A. 74:5463–5467). One of the colonies was selected and the vector was designated pCiP. The peroxidase cDNA fragment was excised from the vector by cleavage with BamHI/XhoI and was purified by agarose gel electrophoresis, electroeluted and made ready for ligation reactions. The cDNA fragment was ligated to BamHI/XhoI digested pHD414 to generate pJVi9 wherein the cDNA was under transcriptional control of the TAKA promoter from Aspergillus oryzae and the AMG™ (Novo Nordisk A/S, Bagsværd, Denmark) terminator from Aspergillus niger as shown in FIG. 8.

Figure 9:
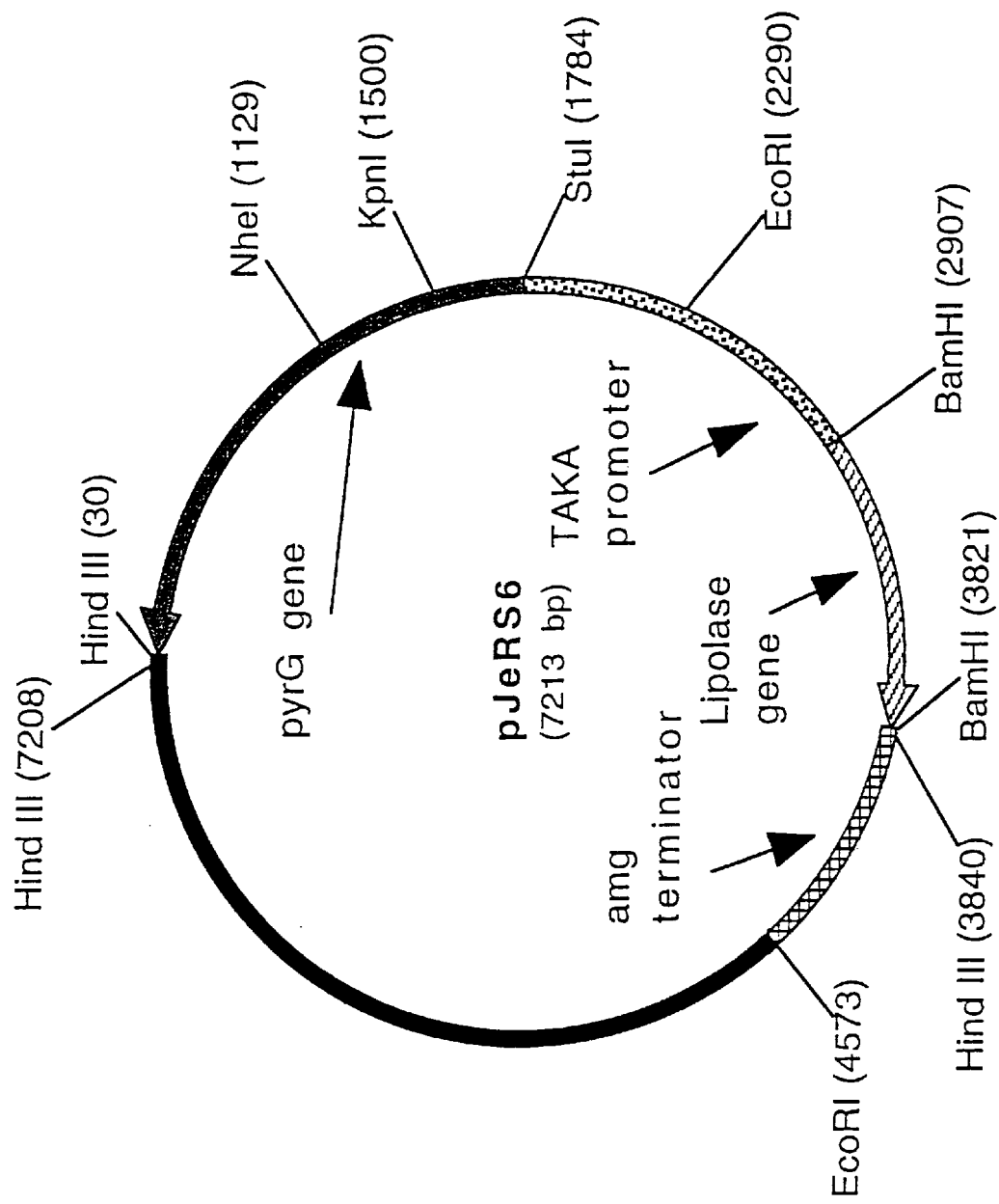
FIG. 9 shows a restriction map of plasmid pJeRS6.
Figure 10:
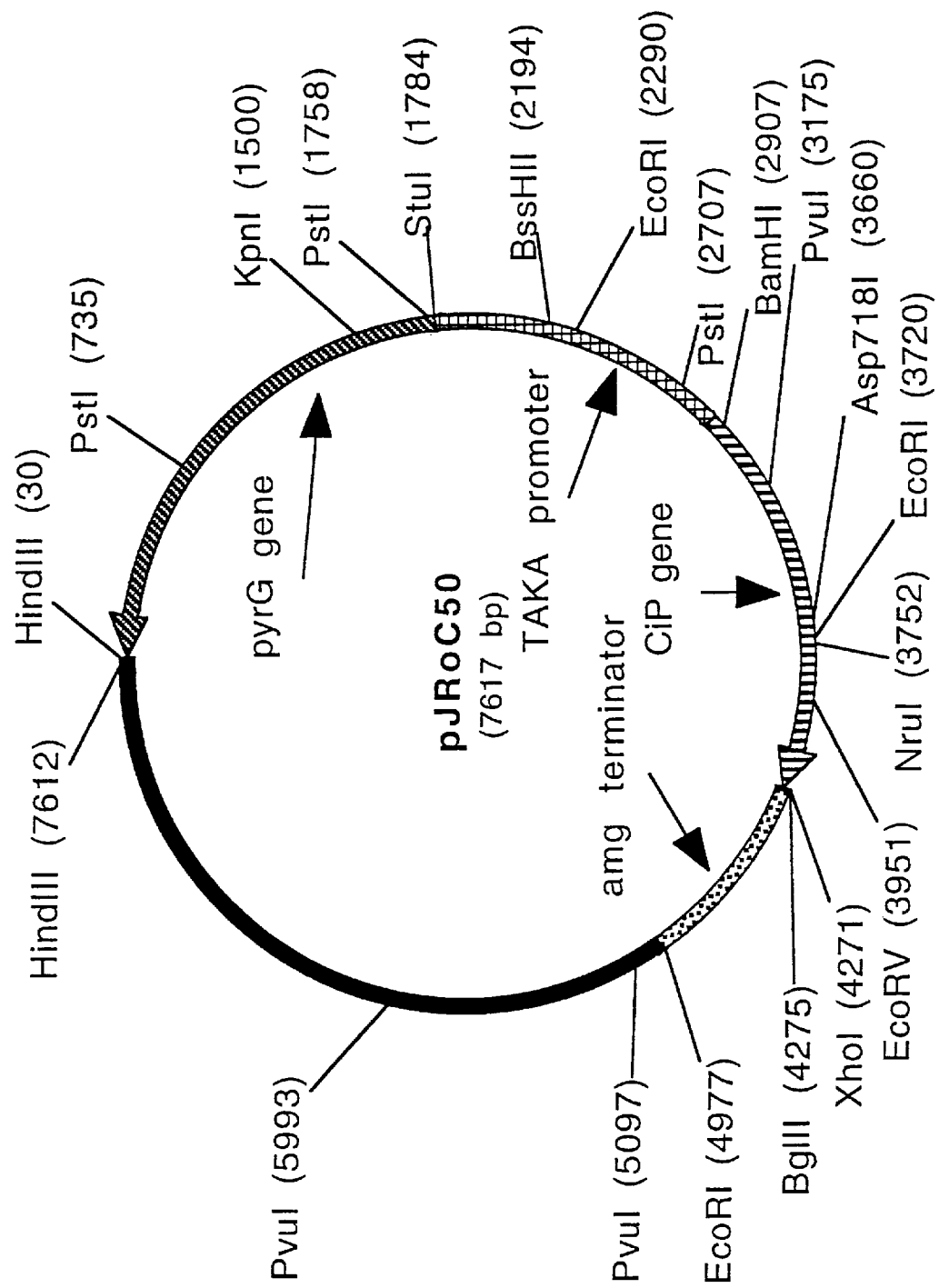
FIG. 10 shows a restriction map of plasmid pJRoC50.

The cDNA encoding the Coprinus cinereus peroxidase was excised from plasmid pJVi9 as a BamHI-XhoI fragment and cloned into plasmid pJeRS6 (FIG. 9) to produce plasmid pJRoC50 (FIG. 10) which contains pyrG as a selectable marker, the TAKA promoter, and the amdS terminator.

Transformants of Aspergillus oryzae strain HowB425 were made using 5 μg of purified plasmid pJRoC50 as described below with the following changes. The agar overlay was omitted and the protoplasts were plated directly on Minimal Medium plates. The transformation was conducted with protoplasts at a concentration of $2 \times 10^7$ protoplasts per ml. One hundred μl of protoplasts were placed on ice with 5 μg DNA for 30 minutes. One ml of SPTC (40% PEG 4000, 0.8 M sorbitol, 0.05 M Tris pH 8.0, 0.05 M $CaCl_2$) was added and the protoplasts were incubated at 34° C. for 20 minutes. The transformation was plated directly onto plates containing Minimal medium. The Minimal medium (pH 6.5) was composed of 6 g of $NaNO_3$, 0.52 g of KCl, 1.52 g of $KH_2PO_4$, 1 ml of trace metals, 1 g of glucose, 500 mg of $MgSO_4 \cdot 7H_2O$, 342.3 g of sucrose, and 20 g of Noble agar per liter. The trace metals solution (1000X) was composed of 22 g of $ZnSO_4$-$7H_2O$, 11 g of $H_3BO_3$, 5 g of $MnCl_2$-$4H_2O$, 5 g of $FeSO_4$-$7H_2O$, 1.6 g of $CoCl_2$-$5H_2O$, 1.6 g of $(NH_4)_6Mo_7O_{24}$, and 50 g of $Na_4EDTA$ per liter. Plates were incubated 5–7 days at 34° C. Transformants were transferred to plates of the same medium and incubated 3–5 days at 37° C.

Sixty-six transformants were assayed for peroxidase activity using the following enzyme assay: 180 μl of substrate buffer {20 ml of 0.1 M potassium phosphate-0.01% Tween-80 pH 7.0, 250 μl of 2,2'-azinobis(3-ethylbenzothiazoline-6-sulfonate) (ABTS) solution (22 mg/ml), and 2 μl of 30% hydrogen peroxide} were added to 20 μl of culture supernatant which was diluted 1:900, quickly followed by measurement of the absorbance at 405 nm at 25° C. using a Molecular Devices Thermomax Microplate Reader (Molecular Devices, Sunnyvale, Calif.). Measurements were recorded every 10 seconds over a 2 minute period with mixing and $V_{max}$ values were calculated using the SOFTmax program (Molecular Devices, Sunnyvale, Calif.). The peroxidase units (POXU) per ml were estimated using a standard curve constructed with a known amount of *Cinereus coprinus* peroxidase as a standard. A POXU was defined as the amount of enzyme that catalyzes the conversion of 1.0 μmole per minute of 0.88 mM $H_2O_2$, 1.67 mM ABTS, 0.1 M phosphate pH 7.0 at 30° C. The four transformants expressing the highest levels were spore purified by streaking spores and picking isolated colonies using the same plates under the same conditions described above.

Final evaluations were performed in shake flasks where approximately 5×10⁶ spores of each transformant were inoculated into 25 ml of MY25 medium containing 1% yeast extract, 2.5% maltose, 0.2% urea, and 1X MY salts pH 6.5. 1X MY salts was composed of 2 g of $MgSO_4$-$7H_2O$, 2 g of $K_2PO_4$, 10 g of $KH_2PO_4$, 2 g of citric acid, 0.5 ml of trace metals solution and 1 ml of 10% $CaCl_2$-$2H_2O$ per liter. The trace metals solution was composed of 13.9 g of $FeSO_4$-$7H_2O$, 8.5 g of $MnSO_4$-$H_2O$, 14.28 g of $ZnSO_4$-$7H_2O$, 1.63 g of $CuSO_4$, 0.24 g of $NiCl_2$-$6H_2O$, and 3.0 g of citric acid per liter. Hemin was added to a final concentration of 0.01 mg/ml from a fresh 10 mg/ml stock prepared in 50 mM NaOH. The shake flasks were incubated at 34° C. and 200 rpm for 7 to 8 days. The best peroxidase producer was designated JRoC50.3.18A.

Example 8

Transformation of *Aspergillus oryzae* JRoC50.3.18A with pSE31

*Aspergillus oryzae* strain JRoC50.3.18A was transformed with pSE31 in order to determine whether overexpression of the hemA gene increased peroxidase production.

The transformation was conducted with protoplasts at a concentration of 2×10⁷ protoplasts per ml. One hundred μl of protoplasts were incubated at 34° C. with 10 μg DNA and 200 μl of 60% PEG 4000-10 mM HEPES-10 mM $CaCl_2$ solution for 30 minutes. Three ml of SPTC (40% PEG 4000, 0.8 M sorbitol, 0.05 M Tris pH 8.0, 0.05 M $CaCl_2$) were added and the protoplasts were plated directly onto COVE transformation plates (per liter: 0.52 g of KCl, 0.52 g of $MgSO_4$-$7H_2O$, 1.52 g of $KH_2PO_4$, 1 ml of trace metals solution as described in Example 7, 342.3 g of sucrose, 25 g of Noble agar, 10 ml of 1 M acetamide, and 10 ml of 3 M CsCl) for amdS transformations. Plates were incubated 5–7 days at 34° C. Transformants were transferred to plates of the same medium and incubated 3–5 days at 34° C. The transformants were then purified by streaking spores and picking isolated colonies using the same plates under the same conditions.

Example 9

Peroxidase Production by hemA Transformants

The transformants from Example 8 were inoculated into individual wells at approximately 1×10⁵ spores per well of a 24-well microtiter plate containing 1 ml of quarter strength MY25 medium composed of 0.25% yeast extract, 0.63% maltose, and 0.05% urea pH 6.5, and 1X MY salts (see Example 7). The microtiter plates were incubated at 34° C. and 100 rpm in a humidity chamber for 5 days.

Peroxidase production levels were determined using the enzyme assay described in Example 7. The results of the microtiter plate tests demonstrate that the average POXU/ml of hemA transformants was 1.4-fold greater than the average of the vector only transformants, with the best hemA transformant showing a 1.6-fold increase in peroxidase production.

A minority (39%) of the hemA transformants show peroxidase levels similar to the majority of the vector only controls. PCR amplification using 50 ng of genomic DNA isolated as described in Example 1 from each transformant was performed as described in Example 2 except the primers hemA3' (see Example 4) and primer 5'-TCTCTTCCTTCCTGAATCCTC-3' (SEQ ID NO:15) were used. This analysis showed that the hemA transformants contain the expression cassette.

Eleven of the best hemA transformants obtained above were cultivated in shake flasks to better evaluate the effects on peroxidase production. For shake flask evaluations, approximately 5×10⁶ spores of each transformant were inoculated into 25 ml of MY25 medium containing 1% yeast extract, 2.5% maltose, 0.2% urea, and 1X MY salts pH 6.5 (see Example 7). The shake flasks were incubated at 34° C. and 200 rpm for 7 to 8 days. Peroxidase assays were performed as described above.

The results demonstrated that five transformants, SE01–15, SE01–20, SE01–26, SE01–28 and SE01–32, produced peroxidase levels which were greater than the vector alone control strains, with three transformants expressing peroxidase at a level 1.9-fold greater than the average control peroxidase levels. The remaining six hemA transformants showed peroxidase levels which were comparable to control levels.

Transformant SE01–28 and a control strain SE05–18 (pBANe6 vector alone transformant) were grown in 2 liter fermentations using a standard fed-batch protocol which has high maltose syrup as carbon source. The batch and feed were supplemented with $FeCl_3$ to approximately 0.4 mM. Positive dissolved oxygen tension was maintained in both cultures with feed added at a rate of approximately 2 grams saccharide per liter per hour from day three to day eight. This level was reached in a step-wise manner over days two and three. Biomass in both cultures were approximately equal for the duration of the fermentation.

A 2-fold increase in peroxidase activity was observed with SE01–28 over the control strain SE05–18. There was also a 2-fold increase in the polypeptide level for SE01–28 relative to the control strain SE05–18.

The overall results demonstrated that overexpression of the hemA gene resulted in a 2-fold increase in peroxidase yield. The data indicated further that hemA may represent a key regulatory point during heme biosynthesis in filamentous fungi which upon genetic manipulation can improve hemoprotein production in the absence of hemin supplementation.

DEPOSIT OF MICROORGANISMS

The following strain has been deposited according to the Budapest Treaty in the Agricultural Research Service Patent Culture Collection (NRRL), Northern Regional Research Laboratory, 1815 University Street, Peoria, Ill. 61604, U.S.A.

| Strain | Accession Number | Deposit Date |
|---|---|---|
| E. coli DH5α (pSE17) | NRRL B-21563 | April 22, 1996 |

The strain has been deposited under conditions that assure that access to the culture will be available during the pendency of this patent application to one determined by the Commissioner of Patents and Trademarks to be entitled thereto under 37 C.F.R §1.14 and 35 U.S.C. §122. The deposit represents a substantially pure culture of each deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. An isolated nucleic acid fragment comprising a nucleic acid sequence which encodes a 5-aminolevulinic acid synthase obtained from an *Aspergillus oryzae* strain.

2. A nucleic acid fragment according to claim 1, wherein the nucleic acid sequence encodes a 5-aminolevulinic acid synthase obtained from *Aspergillus oryzae* IFO 4177.

3. A nucleic acid fragment according to claim 2, wherein the nucleic acid sequence is set forth in SEQ ID NO:1.

4. A nucleic acid fragment according to claim 1, which is capable of hybridizing under conditions of high stringency with a probe which hybridizes with the nucleic acid sequence set forth in SEQ ID NO:1 under the conditions of high stringency.

5. A nucleic acid construct comprising a nucleic acid fragment of claim 1 operably linked to regulatory regions capable of directing the expression of the 5-aminolevulinic acid synthase in a suitable expression host.

6. A nucleic acid construct according to claim 5, wherein the nucleic acid sequence encodes the 5-aminolevulinic acid synthase of *Aspergillus oryzae* IFO 4177.

7. A nucleic acid construct according to claim 5, wherein the nucleic acid sequence is capable of hybridizing under conditions of high stringency with a probe which hybridizes with the nucleic acid sequence set forth in SEQ ID NO:1 under the conditions of high stringency.

8. A recombinant vector comprising a nucleic acid construct of claim 5.

9. A vector according to claim 8, wherein the nucleic acid sequence is operably linked to a promoter sequence.

10. A vector according to claim 9, further comprising a transcription termination signal.

11. A vector according to claim 9, further comprising a selectable marker.

12. A recombinant host cell comprising the nucleic acid construct of claim 5.

13. A host cell according to claim 12, wherein the nucleic acid construct is contained on a vector.

14. A host cell according to claim 12, wherein the host cell is a bacterial cell.

15. A host cell according to claim 12, wherein the host cell is a fungal cell.

16. A host cell according to claim 15, wherein the fungal cell is a filamentous fungal cell.

17. The host cell according to claim 16, wherein the filamentous fungal cell is a cell of a species of Acremonium, Aspergillus, Fusarium, Humicola, Myceliophthora, Mucor, Neurospora, Penicillium, Thielavia, Tolypocladium, or Trichoderma.

18. A host cell according to claim 17, wherein the filamentous fungal cell is a Fusarium cell.

19. A host cell according to claim 17, wherein the filamentous fingal cell is an Aspergillus cell.

20. A host cell according to claim 15, wherein the fungal cell is a yeast cell.

21. A host cell according to claim 20, wherein the yeast cell is a strain of Saccharonyces or Schizosaccharomyces.

22. A host cell according to claim 12, wherein the nucleic acid construct is integrated into the host cell genome.

23. A method for producing a 5-aminolevulinic acid synthase obtained from an *Aspergillus oryzae* comprising (a) cultivating a host cell comprising a nucleic acid construct comprising a nucleic acid sequence encoding the 5-aminolevulinic acid synthase under conditions conducive to expression of the 5-aminolevulinic acid synthase; and (b) recovering the 5-aminolevulinic acid synthase.

* * * * *

UNITED STATES PATENT AND TRADEMARK OFFICE
CERTIFICATE OF CORRECTION

PATENT NO. : 5,958,747
DATED : September 28, 1999
INVENTOR(S) : Susan L. Elrod, et al.

It is certified that error appears in the above-identified patent and that said Letters Patent is hereby corrected as shown below:

Col. 40, Line 11- delete "*Saccharonyces*" and insert —*Saccharomyces*—

Signed and Sealed this

Sixteenth Day of May, 2000

Attest:

Q. TODD DICKINSON

Attesting Officer

Director of Patents and Trademarks

SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
        (A) LENGTH: 4157 base pairs
        (B) TYPE: nucleic acid
        (C) STRANDEDNESS: single
        (D) TOPOLOGY: linear (xi) SEQUENCE DESCRIPTION: SEQ ID NO:1:

```
ACCATTGACT CTCAAGCTAT GGATCGTGCT CACCGTCTCG GCCAGACAAG ACAGGTCACG    60

GTGTATCGCC TGATTACTCG CGGCACCATT GAGGAGCGTA TTCGCAAGCG AGCTTTGCAG   120

AAGGAGGAAG TGCAGCGTGT CGTCATCTCA GGTGGCGCAG CTGGTGGGGT TGACTTCAAT   180

ACTCGCAACC GCGAGAGCCG AACCAAGGAC ATCGCCATGT GGCTGGCAGA TGATGAACAG   240

GCGGAGCTTA TTGAGCAAAA GGAGAAGGAA GCGCTGGACC GAGGCGAAGT GTTTGGCGCT   300

AGTAAAGGCG GGAAGAAGGC TGCTCAGAAG AGAAAGAGAG ATATCACGCT GGATGATATG   360

TATCATGAAG GTATGTGAAT CTGATCAAAG CTCTTCGTTC CGGGGAGGCT TCTGGAAATA   420

GTACTAACCG CGTCAATCTA TAGGCGAAGG GAACTTTGAC GATGCCAGTG CAAAGCCATC   480

AGGAGCGGCC ACTCCTGTGT CGACTGCAGA GAATTTAGGC ACCCCATCCT CCACGCCAGT   540

TCCTAAACGA GGACGTGGAA GGGGACAGG AAAGGGCACG TCTAAAAGAG CCAAAACTAC    600

CAAGGAGAGA TTACGTCTCA TTGATGGCGA CGGAGGCTTA GGGCCTAGTT GATTTAATCG   660

ATCTGTGCCT CAATAATGGA CACGGCTGGT TATGGTCATG GCGTTCAGAG ATTGCATTTC   720

TTTCCCACCC TTTATCTTTC TTTCTTTCCT CTTAAACCCC TCTTTTTTGT TTTTCTTTTT   780

ATCGGACTTT ACTTGTGGGC AGCTTACGTT CTGCCTTGTA TTAACAGCAT ATATTCCTGA   840

TTCCTGATGT ACGAAGCGAT TTAAGAGTCA TTGAAGACGA AGGATGAAAC CCGTGGTAAT   900

CAGCCGATAA TGGCAAAGAG AAGGAGAAGA AAAAAATCAA GTGCGAGTTT TGAAATTGAT   960

GGCAAGATAG ACATTGTATC CTGTACCTGT TCTTGGGCTG TGACGGGGGG GGTGAAATTG  1020

ACGGTCATCA CCCGGCTATT ATTACTATTG TTGTACTGTA CATCCGGATC CTGCTGGTCT  1080

GTATCTAGTT AGGGCAATAT TCCCCGTCGC CAGGCCTCTT GGGTTATGAA TGATTTCATA  1140

GGTGAAGTTT CGTATCCGTA CGCACCGAGA GATTTCTTAG TATTACTTGT ATTATGAAAA  1200
```

```
TGCACTTGCC GAGTTAAGTC CGCCGGCCAA TCACGGCGGA GGATATGGTA AGCCGAAAAG   1260

TCTCGCCGAA GTCCCCGACT TACTCTTACT GGAAGTGGCT TAGTGCCCTC AGCGCCCCCT   1320

CGCCCTCAGT CCATCAGCCA GATTGACTCT TATTTCTCTC TCCTCTTCGC CGCGGGTGAC   1380

ATATCCCTCT CCTTCTCCCT CTCCCTCTTG ACAACATTTC ATCTTCGCTT CCTTTTGTGA   1440

TATAGTCAGT TTCGCTATCC ATTGAAGCAT CACTCATGGA GTCTCTTCTC CAGCAGTCCC   1500

GGGCGATGTG CCCGTTCCTT AAGCGCACAT CTCCATCTTC TCTGCGTACG CTGGCAACCG   1560

CGACTCGACC TAGCACTAGT TCCGGTGGAG GCACTATGTC TAATCTCCAG GTCATTGCCC   1620

GTCGCTGCCC TGTCATGAGC AAGGCTCTGG CCGTGCAGAG CGCTCGCATG GCCGGTACCA   1680

AAAGATTCAC CTCATGTGCT GCCGGCATCA CCGGTCTCGG CAACAAGCAT TGCCGTGCTC   1740

CTACTGGGAA GAGAACCCTG CACTCCACCT CCGGTAACGG CGCCAATGTG AGCGCAGAGA   1800

TCTACAAGAA CACCCAGCGA GATCCCGCCG GTTTCTCGAA GATCAAGACC CCTGCCAATG   1860

CTACCGCCGC TGCCGCTACG TCTGGCCCTC GTCCAGAGGC TCCCGTGGCG AAGCCTTTCA   1920

ACTACAATTC TTTCTACAAC ACCGAATTGG AAAAGAAACA CAAGGACAAG TCGTATCGCT   1980

ATTTCAACAA CATCAATCGT CTCGCTCAGG AGTTTCCCCG GGCTCACACC ACATCTGCCG   2040

AGGAACGTGT GACGGTCTGG TGCTCGAACG ATTATCTCGG CATGGGCCGC AACCCCGAGG   2100

TTCTGGCCAC CATGCATAAG ACATTGGACA CCTACGGAGC CGGTGCGGGA GGTACTCGCA   2160

ACATTTCAGG TCACAATCAA CATGCCGTGA GCCTGGAGAA CACCCTGGCC AAATTGCACG   2220

GCAAGGAGGC GGCATTAGTC TTCAGCTCAT GCTTCGTGGC TAACGATGCC ACCCTCGCAA   2280

CCCTGGGTAG CAAGTTGCCC GACTGTGTTA TTCTGTCCGA TAGCCTGAAT CATGCATCGA   2340

TGATTCAGGG TATTCGCCAT TCAGGCGCCA AGAAAATGGT TTTCAAGCAT AATGATCTGG   2400

TCGACCTTGA GGCCAAGTTG GCAGCTCTAC CTCTTCATGT CCCCAAGATT ATTGCATTCG   2460

AATCAGTTTA TAGCATGTGC GGATCTATTG CCCCAATTGA AGAGATCTGT GATCTTGCAG   2520

ACAAGTACGG TGCCATTACT TTCCTGGATG AAGTCCACGC TGTGGGAATG TACGGACCTC   2580

ACGGAGCAGG TGTGGCAGAG CACCTTGACT ATGACATCTA TGCTTCCCAA GATACGGTCA   2640

ACCCGCGCAG TACTAAGGGA ACCGTGATGG ACCGAATCGA TATTATCACC GGTACTCTGG   2700

GCAAGGCCTA CGGATGTGTC GGGGGCTACA TTGCTGGATC CGCTGCGATG GTTGACACCA   2760

TCCGCTCCCT CGCCCCTGGC TTCATCTTCA CCACGTCCTT GCCGCCCGCC ACCATGGCTG   2820

GTGCAGACAC TGCTATCCAG TACCAGGCTC GTCACCAGGG CGACCGCGTC CTGCAGCAGT   2880

TGCACACCCG CGCGGTCAAA GCAGCTTTCA AGGAGTTGGA TATTCCTGTA ATTCCCAACC   2940

CCTCCCATAT CATTCCGCTC CTGGTTGGGG ATGCCGAGGT TGCTAAGAAG GCCTCGGACA   3000

AGCTTCTGGA GGAGCATGGA ATTTATGTAC AAGCCATCAA CTACCCAACC GTGCCTCGGG   3060

GTGAAGAGCG GCTTCGTATC ACGCCCACCC CGGGACATAT CAAGGAGCAC CGCGACCACC   3120

TGGTGCAAGC CGTCCAAACA GTCTGGAACG AACTGGGCAT CAAACGCACC AGCGATTGGG   3180

AAGCGCAAGG CGGCTTCGTC GGCGTGGGTG TCGATGGCGC CGAGGCTGAG AACCAGCCGA   3240

TTTGGAATGA TGTGCAGCTG GGGCTGAAGG AAAACGAAGC CATTGAGGCT GCTGTGGAAC   3300

GCGAGTTTGC CGAGGCCCCC ATGCGGACCG CCACCCGTCC TGCCGCGGCT GCTGCTTCGT   3360

CAATCCCGGT GGGTGTGGCT GCCTGAAGTG GCTGCCCGCA TGTGAGCTGA AATCGACGTG   3420

GAATTCTATA CACACACACA CACACACACA CACACACACA CACACACACA CACACACACA   3480

CACACACACA CACACACACT AACACACACT ATGTTATAAA TTCCACATCC ACTCCTTTGT   3540

CCCTTGTTGG ACGTAATTGG TATTTGGACT ATTAGTTAGA ACCAGTCAGT CGTTACCATG   3600
```

```
TGTTTCGGTT CGACTCGAAA TCTGACATGT TGTCTGCCCC CATGCCACTT CATCTCCTCC    3660

GTAACCGCAG GGCTTCAAAT ACACTGCCCA GTAATTGTAG TCAATATAGC AGTTAACTAA    3720

CCTTCACCAA TTTCCTAATA ACAATAGAAG GGGCCATACA CGCAGTACCA AAGATCACCT    3780

ACCTCCGATC AATATCCGAA CCTCAGGCTA CATACATCAA GTCGCATTAA TCGATTCCGA    3840

CCTCTGTTTA TCCCTGAAAA TAACTAAGAT CATGATCTAC GTTTGGTAAG TGGGACACCT    3900

ACCTACACTG GGAGGTATTG AATAAAGGCA TCATTCATAT AGTCACAAGA TGCCAGGGCC    3960

AATTCATGAT ATGGATAGCT ACTTCCAAAC ATAATTCAGA GGTATCATTC TGCTCTTCAG    4020

ACAGTTCTTC TCGAAGATCA GTAGGAGCCA GTTTTGACCA TTAACTTGTA ATGTAATTGC    4080

GATTGTAGTA GATCCGAGAT CCATTCACTT TCTAAGGGTT AATTGATTCA TTTTACTGAT    4140

ACCTCACCCA CCATATT                                                   4157
```

(2) INFORMATION FOR SEQ ID NO:2:

(i) SEQUENCE CHARACTERISTICS:
        (A) LENGTH: 636 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:2:

```
Met Glu Ser Leu Leu Gln Gln Ser Arg Ala Met Cys Pro Phe Leu Lys
 1               5                  10                  15

Arg Thr Ser Pro Ser Ser Leu Arg Thr Leu Ala Thr Ala Thr Arg Pro
            20                  25                  30

Ser Thr Ser Ser Gly Gly Gly Thr Met Ser Asn Leu Gln Val Ile Ala
        35                  40                  45

Arg Arg Cys Pro Val Met Ser Lys Ala Leu Ala Val Gln Ser Ala Arg
    50                  55                  60

Met Ala Gly Thr Lys Arg Phe Thr Ser Cys Ala Ala Gly Ile Thr Gly
65                  70                  75                  80

Leu Gly Asn Lys His Cys Arg Ala Pro Thr Gly Lys Arg Thr Leu His
                85                  90                  95

Ser Thr Ser Gly Asn Gly Ala Asn Val Ser Ala Glu Ile Tyr Lys Asn
            100                 105                 110

Thr Gln Arg Asp Pro Ala Gly Phe Ser Lys Ile Lys Thr Pro Ala Asn
        115                 120                 125

Ala Thr Ala Ala Ala Thr Ser Gly Pro Arg Pro Glu Ala Pro Val
    130                 135                 140

Ala Lys Pro Phe Asn Tyr Asn Ser Phe Tyr Asn Thr Glu Leu Glu Lys
145                 150                 155                 160

Lys His Lys Asp Lys Ser Tyr Arg Tyr Phe Asn Asn Ile Asn Arg Leu
                165                 170                 175

Ala Gln Glu Phe Pro Arg Ala His Thr Thr Ser Ala Glu Glu Arg Val
            180                 185                 190

Thr Val Trp Cys Ser Asn Asp Tyr Leu Gly Met Gly Arg Asn Pro Glu
        195                 200                 205

Val Leu Ala Thr Met His Lys Thr Leu Asp Thr Tyr Gly Ala Gly Ala
    210                 215                 220

Gly Gly Thr Arg Asn Ile Ser Gly His Asn Gln His Ala Val Ser Leu
225                 230                 235                 240
```

```
Glu Asn Thr Leu Ala Lys Leu His Gly Lys Glu Ala Ala Leu Val Phe
                245                 250                 255

Ser Ser Cys Phe Val Ala Asn Asp Ala Thr Leu Ala Thr Leu Gly Ser
            260                 265                 270

Lys Leu Pro Asp Cys Val Ile Leu Ser Asp Ser Leu Asn His Ala Ser
        275                 280                 285

Met Ile Gln Gly Ile Arg His Ser Gly Ala Lys Met Val Phe Lys
    290                 295                 300

His Asn Asp Leu Val Asp Leu Glu Ala Lys Leu Ala Leu Pro Leu
305                 310                 315                 320

His Val Pro Lys Ile Ile Ala Phe Glu Ser Val Tyr Ser Met Cys Gly
                325                 330                 335

Ser Ile Ala Pro Ile Glu Lys Ile Cys Asp Leu Ala Asp Lys Tyr Gly
                340                 345                 350

Ala Ile Thr Phe Leu Asp Glu Val His Ala Val Gly Met Tyr Gly Pro
            355                 360                 365

His Gly Ala Gly Val Ala Glu His Leu Asp Tyr Asp Ile Tyr Ala Ser
        370                 375                 380

Gln Asp Thr Val Asn Pro Arg Ser Thr Lys Gly Thr Val Met Asp Arg
385                 390                 395                 400

Ile Asp Ile Ile Thr Gly Thr Leu Gly Lys Ala Tyr Gly Cys Val Gly
                405                 410                 415

Gly Tyr Ile Ala Gly Ser Ala Ala Met Val Asp Thr Ile Arg Ser Leu
            420                 425                 430

Ala Pro Gly Phe Ile Phe Thr Thr Ser Leu Pro Pro Ala Thr Met Ala
        435                 440                 445

Gly Ala Asp Thr Ala Ile Gln Tyr Gln Ala Arg His Gln Gly Asp Arg
    450                 455                 460

Val Leu Gln Gln Leu His Thr Arg Ala Val Lys Ala Phe Lys Glu
465                 470                 475                 480

Leu Asp Ile Pro Val Ile Pro Asn Pro Ser His Ile Ile Pro Leu Leu
            485                 490                 495

Val Gly Asp Ala Glu Val Ala Lys Lys Ala Ser Asp Lys Leu Leu Glu
        500                 505                 510

Glu His Gly Ile Tyr Val Gln Ala Ile Asn Tyr Pro Thr Val Pro Arg
    515                 520                 525

Gly Glu Glu Arg Leu Arg Ile Thr Pro Thr Pro Gly His Ile Lys Glu
    530                 535                 540

His Arg Asp His Leu Val Gln Ala Val Gln Thr Val Trp Asn Glu Leu
545                 550                 555                 560

Gly Ile Lys Arg Thr Ser Asp Trp Glu Ala Gln Gly Gly Phe Val Gly
                565                 570                 575

Val Gly Val Asp Gly Ala Glu Ala Glu Asn Gln Pro Ile Trp Asn Asp
            580                 585                 590

Val Gln Leu Gly Leu Lys Glu Asn Glu Ala Ile Glu Ala Ala Val Glu
        595                 600                 605

Arg Glu Phe Ala Glu Ala Pro Met Arg Thr Ala Thr Arg Pro Ala Ala
    610                 615                 620

Ala Ala Ala Ser Ser Ile Pro Val Gly Val Ala Ala
625                 630                 635
```

(2) INFORMATION FOR SEQ ID NO:3:

(i) SEQUENCE CHARACTERISTICS:

(A) LENGTH: 31 base pairs
            (B) TYPE: nucleic acid
            (C) STRANDEDNESS: single
            (D) TOPOLOGY: linear (xi) SEQUENCE DESCRIPTION: SEQ ID NO:3:

TTTATGATGG AGGCCCTTCT CCAGCAGTCT C                               31

(2) INFORMATION FOR SEQ ID NO:4:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (xi) SEQUENCE DESCRIPTION: SEQ ID NO:4:

CTATGCATTT AAGCAGCAGC CGCGACTGG                                  29

(2) INFORMATION FOR SEQ ID NO:5:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (xi) SEQUENCE DESCRIPTION: SEQ ID NO:5:

TCATTTAAAT GATGGAGTCT CTTCTCC                                    27

(2) INFORMATION FOR SEQ ID NO:6:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (xi) SEQUENCE DESCRIPTION: SEQ ID NO:6:

TCTTAATTAA TCAGCTCACA TGCGGG                                     26

(2) INFORMATION FOR SEQ ID NO:7:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (xi) SEQUENCE DESCRIPTION: SEQ ID NO:7:

GCGCGAATTC GTNGGNATNG GNATNAAYCA YGG                             33

(2) INFORMATION FOR SEQ ID NO:8:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (xi) SEQUENCE DESCRIPTION: SEQ ID NO:8:

GCGGATCCGG NGGRCARTTN GACAT                                      25

(2) INFORMATION FOR SEQ ID NO:9:

(i) SEQUENCE CHARACTERISTICS:
            (A) LENGTH: 28 base pairs
            (B) TYPE: nucleic acid (C) STRANDEDNESS: single
        (D) TOPOLOGY: linear (xi) SEQUENCE DESCRIPTION: SEQ ID NO:9:

GCGAATTCAC NCCNCARGTN TTYGAYAC                                           28

(2) INFORMATION FOR SEQ ID NO:10:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:10:

GCGGATCCRA AYTCNCCNGG RAANGG                                             26

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:11:

GCGCGAATTC TGGCARTCNA C                                                  21

(2) INFORMATION FOR SEQ ID NO:12:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:12:

GCGCGAATTC TGGCARAGNA TG                                                 22

(2) INFORMATION FOR SEQ ID NO:13:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:13:

GGATCCGACA TYTTNGCCAT NGC                                                23

(2) INFORMATION FOR SEQ ID NO:14:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:14:

GTYTCRATRT AGAAYTG                                                       17

(2) INFORMATION FOR SEQ ID NO:15:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

TCTCTTCCTT CCTGAATCCT C                                    21

(2) INFORMATION FOR SEQ ID NO:16:

(i) SEQUENCE CHARACTERISTICS:
        (A) LENGTH: 649 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:16:

```
Met Glu Ala Leu Leu Gln Gln Ser Arg Ala Met Cys Pro Phe Leu Lys
  1               5                  10                  15

Arg Ser Ser Pro Asn Thr Leu Arg Ser Leu Ala Thr Ala Thr Arg Pro
             20                  25                  30

Ser Thr Ser Pro Gly Gly Gly Thr Met Thr Asn Leu Gln Arg Ile Ala
         35                  40                  45

Arg Arg Cys Pro Val Met Ser Lys Ala Leu Ala Val Gln Ser Ala Arg
     50                  55                  60

Met Thr Gly Thr Lys Arg Phe Thr Ser Ser Ala Ala Gly Val Pro Gly
 65                  70                  75                  80

Ala Gly Ala Gly Thr Pro Lys Pro Thr Arg Gly Ser Pro Gly Lys Arg
                 85                  90                  95

Ala Leu His Ser Thr Gly Gly Asn Gly Ala Asn Met Ser Thr Glu Phe
            100                 105                 110

His Lys Gly Ala Gln Gln Ile His Pro Gly Leu Ser Asn Ala Thr Arg
        115                 120                 125

Ser His Val Gly Ala Ser Ala Thr Val Ser Gly Pro Thr Pro Arg Ala
    130                 135                 140

Pro Val Ala Ala Pro Phe Asp Tyr Asp Ala Phe Tyr Asn Ala Glu Leu
145                 150                 155                 160

Gln Lys Lys His Gln Asp Lys Ser Tyr Arg Tyr Phe Asn Asn Ile Asn
                165                 170                 175

Arg Leu Ala Gln Glu Phe Pro Arg Ala His Thr Ala Ser Lys Asp Glu
            180                 185                 190

Lys Val Thr Val Trp Cys Ser Asn Asp Tyr Leu Gly Met Gly Arg Asn
        195                 200                 205

Pro Glu Val Leu Ala Thr Met His Lys Thr Leu Asp Thr Tyr Gly Ala
    210                 215                 220

Gly Ala Gly Gly Thr Arg Asn Ile Ser Gly His Asn Gln His Ala Val
225                 230                 235                 240

Ser Leu Glu Asn Thr Leu Ala Lys Leu His Gly Lys Glu Ala Ala Leu
                245                 250                 255

Val Phe Ser Ser Cys Phe Val Ala Asn Asp Ala Thr Leu Ala Thr Leu
            260                 265                 270

Gly Ser Lys Met Pro Asp Cys Val Ile Leu Ser Asp Ser Leu Asn His
        275                 280                 285

Ala Ser Met Ile Gln Gly Ile Arg His Ser Gly Arg Lys Lys Met Val
    290                 295                 300

Phe Lys His Asn Asp Leu Val Asp Leu Glu Thr Lys Leu Ala Ser Leu
305                 310                 315                 320
```

```
Pro Leu His Val Pro Lys Ile Ile Ala Phe Glu Ser Val Tyr Ser Met
            325                 330                 335

Cys Gly Ser Ile Ala Pro Ile Glu Ala Ile Cys Asp Leu Ala Asp Lys
            340                 345                 350

Tyr Gly Ala Ile Thr Phe Leu Asp Glu Val His Ala Val Gly Met Tyr
            355                 360                 365

Gly Pro His Gly Ala Gly Val Ala Glu His Leu Asp Tyr Glu Ile Tyr
            370                 375                 380

Ala Ser Gln Asp Thr Ala Asn Pro Leu Ser Thr Lys Gly Thr Val Met
385                 390                 395                 400

Asp Arg Ile Asn Ile Ile Thr Gly Thr Leu Gly Lys Ala Tyr Gly Cys
                405                 410                 415

Val Gly Gly Tyr Ile Ala Gly Ser Ala Ala Leu Val Asp Thr Ile Arg
            420                 425                 430

Ser Leu Ala Pro Gly Phe Ile Phe Thr Thr Ser Leu Pro Pro Ala Thr
            435                 440                 445

Met Ala Gly Ala Asp Thr Ala Ile Arg Tyr Gln Ala Arg His Gln Gln
            450                 455                 460

Asp Arg Ile Leu Gln Gln Leu His Thr Arg Ala Val Lys Gln Ser Phe
465                 470                 475                 480

Lys Asp Leu Asp Ile Pro Val Ile Pro Asn Pro Ser His Ile Val Pro
                485                 490                 495

Leu Leu Val Gly Asp Ala Glu Leu Ala Lys Gln Ala Ser Asp Lys Leu
            500                 505                 510

Leu Glu Glu His Gly Ile Tyr Val Gln Ala Ile Asn Tyr Pro Thr Val
            515                 520                 525

Pro Arg Gly Glu Glu Arg Leu Arg Ile Thr Pro Thr Pro Gly His Thr
            530                 535                 540

Gln Glu Leu Arg Asp His Leu Val Glu Ala Val Asn Thr Val Trp Asn
545                 550                 555                 560

Asp Leu Gly Ile Lys Arg Ala Ser Asp Trp Lys Ala Met Gly Gly Phe
                565                 570                 575

Val Gly Val Gly Val Glu Ala Ala Glu Leu Glu Asn Gln Pro Ile Trp
            580                 585                 590

Thr Asp Ala Gln Leu Asn Met Arg Pro Asp Glu Thr Leu Glu Ala Ala
            595                 600                 605

Val Glu Arg Glu Phe Gln Ala Ala Val Pro Gly Met Lys Ala Gly Gly
            610                 615                 620

Ala Lys Ala Lys Pro Val Gly Ser Ile Ala Ala Asn Pro Ile Gly Ala
625                 630                 635                 640

Ser Ile Pro Val Ala Ala Ala Glx
                645

(2) INFORMATION FOR SEQ ID NO:17:

(i) SEQUENCE CHARACTERISTICS:
        (A) LENGTH: 548 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:17:

Met Gln Arg Ser Ile Phe Ala Arg Phe Gly Asn Ser Ser Ala Ala Val
1               5                   10                  15

Ser Thr Leu Asn Arg Leu Ser Thr Thr Ala Ala Pro His Ala Lys Asn
```

```
                20                  25                  30
Gly Tyr Ala Thr Ala Thr Gly Ala Gly Ala Ala Ala Thr Ala Thr
        35                  40                  45
Ala Ser Ser Thr His Ala Ala Ala Ala Ala Ala Ala Asn His
50                  55                  60
Ser Thr Gln Glu Ser Gly Phe Asp Tyr Gly Leu Ile Asp Ser Glu
65                  70                  75                  80
Leu Gln Lys Lys Arg Leu Asp Lys Ser Tyr Arg Tyr Phe Asn Asn Ile
                85                  90                  95
Asn Arg Leu Ala Lys Glu Phe Pro Leu Ala His Arg Gln Arg Glu Ala
                100                 105                 110
Asp Lys Val Thr Val Trp Cys Ser Asn Asp Tyr Leu Ala Leu Ser Lys
                115                 120                 125
His Pro Glu Val Leu Asp Ala Met His Lys Thr Ile Asp Lys Tyr Gly
        130                 135                 140
Cys Gly Ala Gly Gly Thr Arg Asn Ile Ala Gly His Asn Ile Pro Thr
145                 150                 155                 160
Leu Asn Leu Glu Ala Glu Leu Ala Thr Leu His Lys Lys Glu Gly Ala
                165                 170                 175
Leu Val Phe Ser Ser Cys Tyr Val Ala Asn Asp Ala Val Leu Ser Leu
                180                 185                 190
Leu Gly Gln Lys Met Lys Asp Leu Val Ile Phe Ser Asp Glu Leu Asn
                195                 200                 205
His Ala Ser Met Ile Val Gly Ile Lys His Ala Asn Val Lys Lys His
                210                 215                 220
Ile Phe Lys His Asn Asp Leu Asn Glu Leu Glu Gln Leu Leu Gln Ser
225                 230                 235                 240
Tyr Pro Lys Ser Val Pro Lys Leu Ile Ala Phe Glu Ser Val Tyr Ser
                245                 250                 255
Met Ala Gly Ser Val Ala Asp Ile Glu Lys Ile Cys Asp Leu Ala Asp
                260                 265                 270
Lys Tyr Gly Ala Leu Thr Phe Leu Asp Glu Val His Ala Val Gly Leu
        275                 280                 285
Tyr Gly Pro His Gly Ala Gly Val Ala Glu His Cys Asp Phe Glu Ser
        290                 295                 300
His Arg Ala Ser Gly Ile Ala Thr Pro Lys Thr Asn Asp Lys Gly Gly
305                 310                 315                 320
Ala Lys Thr Val Met Asp Arg Val Asp Met Ile Thr Gly Thr Leu Gly
                325                 330                 335
Lys Ser Phe Gly Ser Val Gly Gly Tyr Val Ala Ala Ser Arg Lys Leu
                340                 345                 350
Ile Asp Trp Phe Arg Ser Phe Ala Pro Gly Phe Ile Phe Thr Thr Thr
                355                 360                 365
Leu Pro Pro Ser Val Met Ala Gly Ala Thr Ala Ala Ile Arg Tyr Gln
        370                 375                 380
Arg Cys His Ile Asp Leu Arg Thr Ser Gln Gln Lys His Thr Met Tyr
385                 390                 395                 400
Val Lys Lys Ala Phe His Glu Leu Gly Ile Pro Val Ile Pro Asn Pro
                405                 410                 415
Ser His Ile Val Pro Val Leu Ile Gly Asn Ala Asp Leu Ala Lys Gln
                420                 425                 430
Ala Ser Asp Ile Leu Ile Asn Lys His Gln Ile Tyr Val Gln Ala Ile
                435                 440                 445
```

-continued

```
Asn Phe Pro Thr Val Ala Arg Gly Thr Glu Arg Leu Arg Ile Thr Pro
        450                 455                 460

Thr Pro Gly His Thr Asn Asp Leu Ser Asp Ile Leu Ile Asn Ala Val
465                 470                 475                 480

Asp Asp Val Phe Asn Glu Leu Gln Leu Pro Arg Val Arg Asp Trp Glu
                485                 490                 495

Ser Gln Gly Gly Leu Leu Gly Val Gly Glu Ser Gly Phe Val Glu Glu
                500                 505                 510

Ser Asn Leu Trp Thr Ser Ser Gln Leu Ser Leu Thr Asn Asp Asp Leu
                515                 520                 525

Asn Pro Asn Val Arg Asp Pro Ile Val Lys Gln Leu Glu Val Ser Ser
        530                 535                 540

Gly Ile Lys Gln
545
```

(2) INFORMATION FOR SEQ ID NO:18:

(i) SEQUENCE CHARACTERISTICS:
        (A) LENGTH: 587 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:18:

```
Met Val Thr Ala Ala Met Leu Leu Gln Cys Cys Pro Val Leu Ala Arg
1               5                   10                  15

Gly Pro Thr Ser Leu Leu Gly Lys Val Val Lys Thr His Gln Phe Leu
                20                  25                  30

Phe Gly Ile Gly Arg Cys Pro Ile Leu Ala Thr Gln Gly Pro Asn Cys
            35                  40                  45

Ser Gln Ile His Leu Lys Ala Thr Lys Ala Gly Gly Asp Ser Pro Ser
        50                  55                  60

Trp Ala Lys Gly His Cys Pro Phe Met Leu Ser Glu Leu Gln Asp Gly
65                  70                  75                  80

Lys Ser Lys Ile Val Gln Lys Ala Ala Pro Glu Val Gln Glu Asp Val
                85                  90                  95

Lys Ala Phe Lys Thr Asp Leu Pro Ser Leu Val Ser Val Ser Ser Leu
            100                 105                 110

Arg Lys Pro Phe Ser Gly Pro Gln Glu Gln Glu Gln Ile Ser Gly Lys
        115                 120                 125

Val Thr His Leu Ile Gln Asn Asn Met Pro Gly Asn Tyr Val Phe Ser
    130                 135                 140

Tyr Asp Gln Phe Phe Arg Asp Lys Ile Met Glu Lys Lys Gln Asp His
145                 150                 155                 160

Thr Tyr Arg Val Phe Lys Thr Val Asn Arg Trp Ala Asp Ala Tyr Pro
                165                 170                 175

Phe Ala Gln His Phe Glu Ala Ser Val Ala Ser Lys Asp Val Ser
            180                 185                 190

Val Trp Cys Ser Asn Asp Tyr Leu Gly Met Ser Arg His Pro Gln Val
        195                 200                 205

Leu Gln Ala Thr Gln Glu Thr Leu Gln Arg His Gly Ala Gly Ala Gly
    210                 215                 220

Gly Thr Arg Asn Ile Ser Gly Thr Ser Lys Phe His Val Glu Leu Glu
225                 230                 235                 240

Gln Glu Leu Ala Glu Leu His Gln Lys Asp Ser Ala Leu Leu Phe Ser
```

-continued

```
                245                 250                 255
Ser Cys Phe Val Ala Asn Asp Ser Thr Leu Phe Thr Leu Ala Lys Ile
            260                 265                 270

Leu Pro Gly Cys Glu Ile Tyr Ser Asp Ala Gly Asn His Ala Ser Met
            275                 280                 285

Ile Gln Gly Ile Arg Asn Ser Gly Ala Ala Lys Phe Val Phe Arg His
            290                 295                 300

Asn Asp Pro Asp His Leu Lys Lys Leu Leu Glu Lys Ser Asn Pro Lys
305                         310                 315                 320

Ile Pro Lys Ile Val Ala Phe Glu Thr Val His Ser Met Asp Gly Ala
                    325                 330                 335

Ile Cys Pro Leu Glu Glu Leu Cys Asp Val Ser His Gln Tyr Gly Ala
                    340                 345                 350

Leu Thr Phe Val Asp Glu Val His Ala Val Gly Leu Tyr Gly Ser Arg
                    355                 360                 365

Gly Ala Gly Ile Gly Glu Arg Asp Gly Ile Met His Lys Ile Asp Ile
            370                 375                 380

Ile Ser Gly Thr Leu Gly Lys Ala Phe Gly Cys Val Gly Gly Tyr Ile
385                         390                 395                 400

Ala Ser Thr Arg Asp Leu Val Asp Met Val Arg Ser Tyr Ala Ala Gly
                    405                 410                 415

Phe Ile Phe Thr Thr Ser Leu Pro Pro Met Val Leu Ser Gly Ala Leu
                    420                 425                 430

Glu Ser Val Arg Leu Leu Lys Gly Glu Glu Gly Gln Ala Leu Arg Arg
                    435                 440                 445

Ala His Gln Arg Asn Val Lys His Met Arg Gln Leu Leu Met Asp Arg
            450                 455                 460

Gly Leu Pro Val Ile Pro Cys Pro Ser His Ile Ile Pro Ile Arg Val
465                         470                 475                 480

Gly Asn Ala Ala Leu Asn Ser Lys Leu Cys Asp Leu Leu Leu Ser Lys
                    485                 490                 495

His Gly Ile Tyr Val Gln Ala Ile Asn Tyr Pro Thr Val Pro Arg Gly
                    500                 505                 510

Glu Glu Leu Leu Arg Leu Ala Pro Ser Pro His His Ser Pro Gln Met
            515                 520                 525

Met Glu Asp Phe Val Glu Lys Leu Leu Leu Ala Trp Thr Ala Val Gly
            530                 535                 540

Leu Pro Leu Gln Asp Val Ser Val Ala Ala Cys Asn Phe Cys Arg Arg
545                         550                 555                 560

Pro Val His Phe Glu Leu Met Ser Glu Trp Glu Arg Ser Tyr Phe Gly
                    565                 570                 575

Asn Met Gly Pro Gln Tyr Val Thr Thr Tyr Ala
            580                 585
```